(12) United States Patent
Watanabe et al.

(10) Patent No.: US 10,845,186 B2
(45) Date of Patent: Nov. 24, 2020

(54) INFORMATION PROCESSING DEVICE, INFORMATION PROCESSING METHOD, AND INFORMATION PROCESSING SYSTEM

(71) Applicant: SONY CORPORATION, Tokyo (JP)

(72) Inventors: Shinji Watanabe, Tokyo (JP); Tomohiro Hayakawa, Saitama (JP)

(73) Assignee: SONY CORPORATION, Tokyo (JP)

( * ) Notice: Subject to any disclaimer, the term of this patent is extended or adjusted under 35 U.S.C. 154(b) by 141 days.

(21) Appl. No.: 16/080,508

(22) PCT Filed: Dec. 29, 2016

(86) PCT No.: PCT/JP2016/089220
§ 371 (c)(1),
(2) Date: Aug. 28, 2018

(87) PCT Pub. No.: WO2017/154318
PCT Pub. Date: Sep. 14, 2017

(65) Prior Publication Data
US 2019/0017811 A1 Jan. 17, 2019

(30) Foreign Application Priority Data
Mar. 9, 2016 (JP) .................. 2016-045380

(51) Int. Cl.
*G01B 11/16* (2006.01)
*C12M 1/34* (2006.01)
(Continued)

(52) U.S. Cl.
CPC .............. *G01B 11/16* (2013.01); *C12M 1/34* (2013.01); *C12Q 1/02* (2013.01); *G01N 33/4833* (2013.01);
(Continued)

(58) Field of Classification Search
CPC . G06T 7/248; G06T 7/20; C12M 1/02; C12M 1/34; G01B 11/16; G01N 33/4833
See application file for complete search history.

(56) References Cited

U.S. PATENT DOCUMENTS 6,993,157 B1 1/2006 Oue et al.
7,079,144 B1 7/2006 Shimada et al.
(Continued)

FOREIGN PATENT DOCUMENTS

CN 102906789 A 1/2013
CN 105378795 A 3/2016
(Continued)

OTHER PUBLICATIONS

Bazan, et al., "Image Processing Techniques for Assessing Contractility in Isolated Adult Cardiac Myocytes", International Journal of Biomedical Imaging, vol. 2009, Article ID 352954, Aug. 24, 2009, 11 pages.
(Continued)

*Primary Examiner* — Leon Flores
(74) *Attorney, Agent, or Firm* — Chip Law Group

(57) ABSTRACT

[Object] To analyze a strain of a biological sample more accurately. [Solution] Provided is an information processing device including: a setting unit configured to set at least one region of interest from one captured image constituting a dynamic image for a biological sample; an analysis object specifying unit configured to specify an analysis object for the at least one region of interest; a detection unit configured to detect a motion of the analysis object in the dynamic image; and an analysis unit configured to analyze a strain of the biological sample related to the at least one region of interest on a basis of the detected motion of the analysis object.

20 Claims, 22 Drawing Sheets

(51) Int. Cl.
  *G06T 7/20* (2017.01)
  *G06T 7/246* (2017.01)
  *C12Q 1/02* (2006.01)
  *G01N 33/483* (2006.01)

(52) U.S. Cl.
  CPC ............... *G06T 7/20* (2013.01); *G06T 7/248* (2017.01); *G06T 2207/20104* (2013.01); *G06T 2207/30024* (2013.01)

(56) References Cited

U.S. PATENT DOCUMENTS

| | | | |
|---|---|---|---|
| 2007/0118041 A1 | 5/2007 | Nishiura et al. | |
| 2013/0070971 A1 | 3/2013 | Kunihiro et al. | |
| 2013/0294675 A1 | 11/2013 | Liu et al. | |
| 2014/0334687 A1* | 11/2014 | Xu | G06T 7/0016 382/107 |
| 2016/0093095 A1* | 3/2016 | Okazaki | G06T 17/20 345/419 |
| 2016/0104296 A1 | 4/2016 | Kunihiro et al. | |

FOREIGN PATENT DOCUMENTS

| | | |
|---|---|---|
| EP | 1139286 A1 | 10/2001 |
| EP | 2845146 A1 | 3/2015 |
| EP | 3022714 A1 | 5/2016 |
| JP | 06-138137 A | 5/1994 |
| JP | 2000-251086 A | 9/2000 |
| JP | 2001-34764 A | 2/2001 |
| JP | 2001-034764 A | 2/2001 |
| JP | 2003-256850 A | 9/2003 |
| JP | 2007-117611 A | 5/2007 |
| JP | 2011-101336 A | 5/2011 |
| JP | 2014-075999 A | 5/2014 |
| JP | 2014-75999 A | 5/2014 |
| JP | 2015-19620 A | 2/2015 |
| JP | 2015-019620 A | 2/2015 |
| JP | 2015-518378 A | 7/2015 |
| WO | 00/51079 A1 | 2/2000 |
| WO | 00/51079 A | 8/2000 |
| WO | 00/51079 A1 | 8/2000 |
| WO | 2000/070558 A1 | 11/2000 |
| WO | 2011/122200 A1 | 10/2011 |
| WO | 2013/165301 A1 | 11/2013 |
| WO | 2015/008459 A1 | 1/2015 |

OTHER PUBLICATIONS

Kamgoue, et al., "Quantification of Cardiomyocyte Contraction Based on Image Correlation Analysis", International Society for Advancement of Cytometry, Jun. 26, 2008, 12 Pages.

Bazan, et al., "Image Processing Techniques for Assessing Contractility in Isolated Adult Cardiac Myocytes", Hindawi Publishing Corporation, International Journal of Biomedical Imaging, vol. 2009, Article ID 352954, 11 pages.

Kamgoue, et al., "Quantification of Cardiomyocyte Contraction Based on Image Correlation Analysis", International Society for Advancement of Cytometry, 2009, Kinematics of Cardiomyocyte Contraction, pp. 298-308.

International Search Report and Written Opinion of PCT Application No. PCT/JP2016/089220, dated Apr. 4, 2017, 11 pages of ISRWO.

* cited by examiner

INFORMATION PROCESSING DEVICE, INFORMATION PROCESSING METHOD, AND INFORMATION PROCESSING SYSTEM

CROSS REFERENCE TO RELATED APPLICATIONS

This application is a U.S. National Phase of International Patent Application No. PCT/JP2016/089220 filed on Dec. 29, 2016, which claims priority benefit of Japanese Patent Application No. JP 2016-045380 filed in the Japan Patent Office on Mar. 9, 2016. Each of the above-referenced applications is hereby incorporated herein by reference in its entirety.

TECHNICAL FIELD

The present disclosure relates to an information processing device, an information processing method, a program, and an information processing system.

BACKGROUND ART

In the fields of medical and life sciences, observation of motions of many types of biological samples and evaluation of changes in a form thereof have been performed. For example, a technique of evaluating a dynamic characteristic (strain) related to contraction or relaxation of a biological sample has been developed. By evaluating a strain in this way, it becomes possible to quantitatively evaluate a dynamic characteristic related to a change in a form of the biological sample.

For example, a method of performing a Fourier series expansion of shape information of a cardiac myocyte obtained by performing a segmentation process on regions of interest in a captured image corresponding to the cardiac myocyte which is an example of a biological sample and analyzing a strain of the cardiac myocytes on the basis of an obtained Fourier descriptor is disclosed in the following Non-Patent Literature 1. Further, a method of detecting a motion inside a biological sample displayed in a captured image using a correlation function, associating the detected motion with a dynamic distortion tensor, and calculating a strain of the biological sample is disclosed in the following Non-Patent Literature 2.

CITATION LIST

Non-Patent Literature

Non-Patent Literature 1, C. Bazan et al. "Image Processing Techniques for Assessing Contractility in Isolated Adult Cardiac Myocytes" International Journal of Biomedical Imaging, 2009, 352954.

Non-Patent Literature 2: A. Kamogue et al. "Quantification of cardiac myocytes contraction based on image correlation analysis." Cytometry Part A, 75A, 2009, p. 298-308.

DISCLOSURE OF INVENTION

Technical Problem

However, in the technique disclosed in Non-Patent Literature 1, it is necessary to perform a process of recognizing a region of interest corresponding to a cardiac myocyte and a segmentation process for the region of interest for each frame of the captured image. Therefore, there is a possibility of a load of a strain analysis process becoming huge. Further, in the technique disclosed in Non-Patent Literature 2, since a region corresponding to the biological sample is not specified, it is difficult to acquire the motion inside the biological sample which changes the form greatly. Therefore, there is a possibility of the accuracy of a strain analysis result decreasing depending on the biological sample to be analyzed.

In this regard, the present disclosure proposes an information processing device, an information processing method, a program, and an information processing system which are novel and improved and capable of analyzing a strain of a biological sample more accurately.

Solution to Problem

According to the present disclosure, there is provided an information processing device including: a setting unit configured to set at least one region of interest from one captured image constituting a dynamic image for a biological sample; an analysis object specifying unit configured to specify an analysis object for the at least one region of interest; a detection unit configured to detect a motion of the analysis object in the dynamic image; and an analysis unit configured to analyze a strain of the biological sample related to the at least one region of interest on a basis of the detected motion of the analysis object.

In addition, according to the present disclosure, there is provided an information processing method including: setting, by a processor, at least one region of interest from one captured image constituting a dynamic image for a biological sample; specifying, by the processor, an analysis object for the at least one region of interest; detecting, by the processor, a motion of the analysis object in the dynamic image; and analyzing, by the processor, a strain of the biological sample related to the at least one region of interest on a basis of the detected motion of the analysis object.

In addition, according to the present disclosure, there is provided a program causing a computer to function as: a setting unit configured to set at least one region of interest from one captured image constituting a dynamic image for a biological sample; an analysis object specifying unit configured to specify an analysis object for the at least one region of interest; a detection unit configured to detect a motion of the analysis object in the dynamic image; and an analysis unit configured to analyze a strain of the biological sample related to the at least one region of interest on a basis of the detected motion of the analysis object.

In addition, according to the present disclosure, there is provided an information processing system including: an imaging device including an imaging unit configured to generate a dynamic image of a biological sample; and an information processing device including a setting unit configured to set at least one region of interest from one captured image constituting the dynamic image, an analysis object specifying unit configured to specify an analysis object for the at least one region of interest, a detection unit configured to detect a motion of the analysis object in the dynamic image, and an analysis unit configured to analyze a strain of the biological sample related to the at least one region of interest on a basis of the detected motion of the analysis object.

Advantageous Effects of Invention

As described above, according to the present disclosure, it is possible to analyze a strain of a biological sample more accurately.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
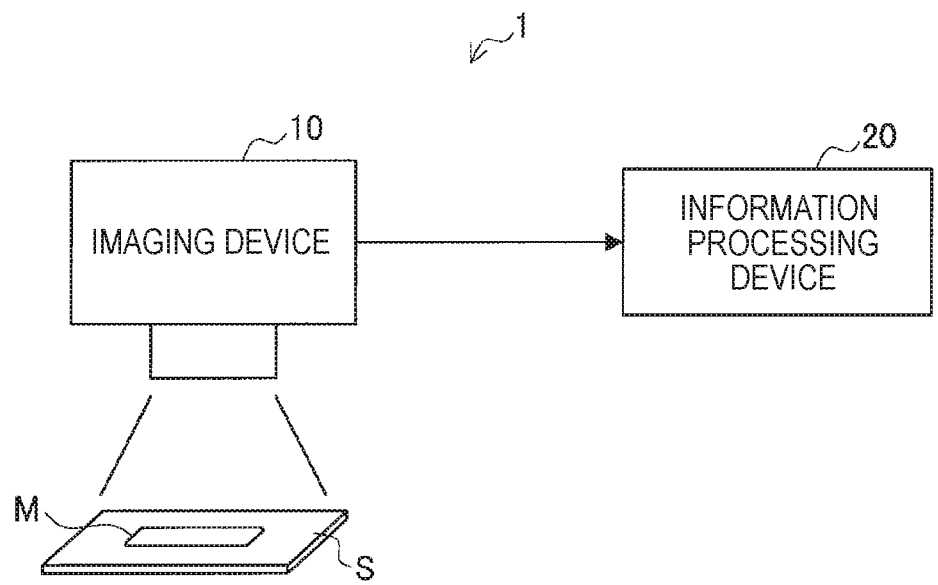
FIG. 1 is a diagram illustrating an overview of a configuration of an information processing system according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.

1. Overview of information processing system
2. Information processing device
2.1. Configuration example
2.2. Process example
2.3. Effect
3. Hardware configuration example
4. Conclusion «1. Overview of Information Processing System»

FIG. 1 is a diagram showing an overview of a configuration of an information processing system 1 according to an embodiment of the present disclosure. As shown in FIG. 1, the information processing system 1 is provided with an imaging device 10 and an information processing device 20. The imaging device 10 and the information processing device 20 are connected to each other via various types of wired or wireless networks.

(Imaging device)

The imaging device 10 is a device which generates captured images (dynamic images). The imaging device 10 according to the present embodiment is realized by, for example, a digital camera. In addition, the imaging device 10 may be realized by any type of device having an imaging function, for example, a smartphone, a tablet, a game device, or a wearable device. The imaging device 10 images real spaces using various members, for example, an image sensor such as a charge coupled device (CCD) or a complementary metal oxide semiconductor (CMOS), a lens for controlling formation of a subject image in the image sensor, and the like. The image sensor and the various members realize the function of the imaging device 10 as an imaging unit. In addition, the imaging device 10 includes a communication device for transmitting and receiving captured images and the like to and from the information processing device 20. In the present embodiment, the imaging device 10 is provided above an imaging stage S to image a culture medium M in which a cell that is an observation object is cultured. Note that the cell is an example of a biological sample. In addition, the imaging device 10 generates dynamic image data by imaging the culture medium M at a specific frame rate. Note that the imaging device 10 may directly image the culture medium M (without involving another member), or may image the culture medium M via another member such as a microscope. In addition, although the frame rate is not particularly limited, it is desirable to set the frame rate according to the degree of a change of the observation object. Note that the imaging device 10 images a given imaging region including the culture medium M in order to accurately track a change of the observation object. Dynamic image data generated by the imaging device 10 is transmitted to the information processing device 20.

Note that, although the imaging device 10 is assumed to be a camera installed in an optical microscope or the like in the present embodiment, the present technology is not limited thereto. For example, the imaging device 10 may be an imaging device included in an electronic microscope using electron beams such as a scanning electron microscope (SEM) or a transmission electron microscope (TEM), or an imaging device included in a scanning probe microscope (SPM) that uses a short hand such as an atomic force microscope (AFM) or a scanning tunneling microscope (STM). In this case, a dynamic image generated by the imaging device 10 is a dynamic image obtained by irradiating the observation object with electron beams in the case of an electronic microscope. In addition, when the imaging device 10 is an SPM, a dynamic image generated by the imaging device 10 is a dynamic image obtained by tracing an observation object using a short hand. These dynamic images can also be analyzed by the information processing device 20 according to the present embodiment.

(Information Processing Device)

The information processing device 20 is a device having an image analyzing function. The information processing device 20 is realized by any type of device having an image analyzing function such as a personal computer (PC), a tablet, or a smartphone. The information processing device 20 includes a processing circuit and a communication device. For example, in the information processing device 20 according to the present embodiment, the communication device acquires the dynamic image from the imaging device 10 and sets at least one region of interest for the dynamic image acquired by the processing circuit. Further, the processing circuit specifies an analysis object for the set region of interest and detects a motion of the analysis object. Further, the processing circuit analyzes the strain of the observation object related to the region of interest on the basis of the motion of the analysis object. The processes performed by the processing circuit of the information processing device 20 are output to a storage device, a display device, or the like provided inside or outside the information processing device 20. Note that the information processing device 20 may be realized by one or a plurality of information processing devices on a network. A functional configuration for realizing the respective functions of the information processing device 20 will be described below.

Note that, although the information processing system 1 is constituted with the imaging device 10 and the information processing device 20 in the present embodiment, the present technology is not limited thereto. For example, the imaging device 10 may perform the processes of the information processing device 20 (for example, a detection process and an analysis process). In this case, the information processing system 1 can be realized by the imaging device having the detection function and the analysis function.

Here, the observation object and the strain of the information processing system 1 according to the present embodiment will be described. First, an observation object according to the present embodiment is mainly a biological sample. A biological sample is an organism which can be observed using an optical microscope or the like, for example, any of various types of cells, cell organelles or biological tissues, or living organisms such as micro-organisms or plankton. A biological sample in the present embodiment in particular is an organism that can move in the culture M on the imaging stage S of the imaging device 10. Such a biological sample will be referred to hereinafter as an observation object.

In particular, the observation object according to the present embodiment may be an observation object that performs periodic movement. The periodic movement may be, for example, movement (a beat) associated with contraction and relaxation by a muscle or the like. Examples of the observation object performing such periodic movement include sarcomeres (sarcomeres) and myogenic fibers, or muscle fibers, muscles, and the like which are configured of sarcomeres. The muscle may be a skeletal muscle or a visceral muscle (in particular, an involuntary muscle such as myocardium). Further, the observation object according to the present embodiment may be a cardiac myocyte that forms myocardium or a vessel such as an artery that beats in accordance with a heartbeat. Further, the application target of the present technology is not limited to observation objects that perform the periodic movement. For example, an observation object that performs contractions and relaxation in response to external stimuli or internal stimuli is included as the application target of the present technology.

Further, in the present embodiment, the observation object is a biological sample, but the present technology is not limited to this example. For example, the observation object may be a structure such as an organism or an inanimate object having a size of a scale of millimeters to nanometers. The information processing system 1 may be used to analyze distortion (corresponding to a strain) related to the change in the form of the observation object as long as it is a structure that performs contraction and relaxation (or elongation).

Next, the strain according to the present embodiment will be described. The strain is an index indicating a dynamic characteristic related to a change in a form of a biological sample (observation object). When the observation object beats, distortion may occur locally in the observation object. The distortion is a strain indicating a local dynamic characteristic of the observation object. By quantifying the strain, it is possible to evaluate a contractile ability of the observation object. For example, in a case in which the observation object is a cardiac myocyte, it is possible to quantitatively evaluate an effect related to a medicine administered to the cardiac myocyte, a contractile ability of the cardiac myocytes prepared using a technique related to a regenerative medicine, and the like.

Figure 2:
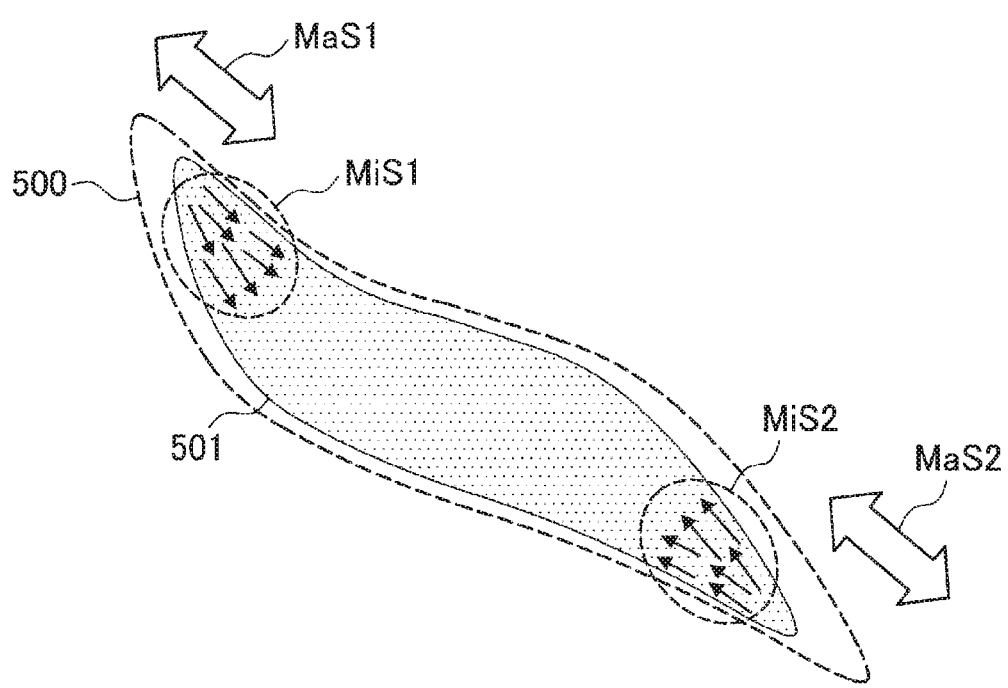
FIG. 2 is a diagram for describing types of strains according to the embodiment.

There are roughly two kinds of strains according to the present embodiment. FIG. 2 is a diagram for describing types of strain according to the present embodiment. Referring to FIG. 2, an observation object 500 contracts and changes its shape as shown by an observation object 501. At this time, there are two types of strains of the observation object 500, that is, macro strains MaS1 and MaS2 indicating a dynamic characteristic related to contraction or relaxation of the entire observation object 500 and micro strains MiS1 and MiS2 indicating a local dynamic characteristic inside the observation object 500.

The macro strains are strains indicating the magnitude of the change in the form of the observation object 500 in an expansion and contraction direction of the observation object 500. In other words, the macro strains are strains calculated on the basis of a difference (distortion) between an original form of the observation object 500 and a form of the observation object 501 contracted from the original form.

On the other hand, the micro strains are strain indicating change amounts in local motions of the observation object 500 that contribute to the movement in the expansion and contraction direction of the observation object 500. In other words, as illustrated in FIG. 2, the micro strains are strains calculated on the basis of changes in individual motions inside the observation object 500 that contribute to the movement in the expansion and contraction direction of the observation object 500.

The macro strains are so-called non-dimensional distortion amounts, whereas the micro strains are values having a dimension of a change amount of motion in two dimensions (that is, corresponding to acceleration). Further, the micro strains according to the present embodiment are vectors (having a size and a direction). According to the information processing system 1 of the present embodiment, it is necessary to complexly evaluate the local dynamic characteristics of the observation object in further detail using at least one of the two types of strains.

The overview of the information processing system 1 according to an embodiment of the present disclosure has been described above. The information processing device 20 included in the information processing system 1 according to an embodiment of the present disclosure is realized in the following embodiment. A specific configuration example and a process example of the information processing device 20 will be described below. Further, in the following description, macro strains and micro strains are referred to collectively as "strains" unless it is particularly necessary to distinguish them.

«2. Information Processing Device»

Hereinafter, the information processing device 20 according to an embodiment of the present disclosure will be described with reference to FIGS. 3 to 24.

<2.1. Configuration Example>

Figure 3:
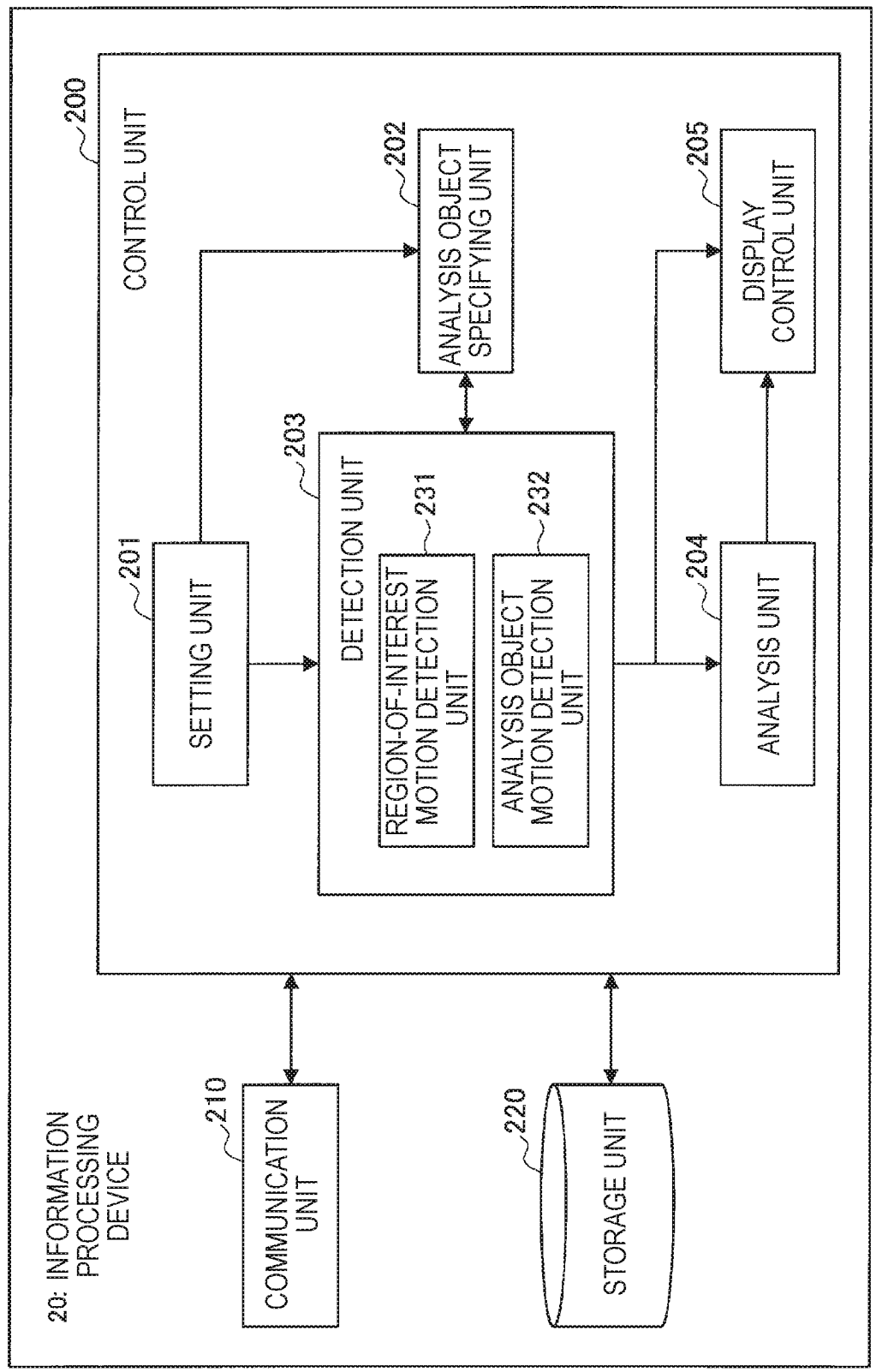
FIG. 3 is a functional block diagram illustrating a functional configuration example of an information processing device according to the embodiment of the present disclosure.

FIG. 3 is a functional block diagram illustrating a functional configuration example of the information processing device 20 according to one embodiment of the present disclosure. As illustrated in FIG. 3, the information processing device 20 according to the present embodiment includes a control unit 200, a communication unit 210, and a storage unit 220. A function of the control unit 200 is implemented by a processing circuit such as a central processing unit (CPU) installed in the information processing device 20. Further, a function of the communication unit 210 is implemented by a communication device installed in the information processing device 20. Further, a function of the storage unit 220 is implemented by a storage device such as a storage installed in the information processing device 20. The respective function units will be described below.

(Control Unit)

The control unit 200 controls the overall operation of the information processing device 20. Further, as illustrated in FIG. 3, the control unit 200 includes functions of a setting unit 201, an analysis object specifying unit 202, a detection unit 203, an analysis unit 204, and a display control unit 205, and undertakes an operation of the information processing device 20 according to the present embodiment. The functions of the respective function units installed in the control unit 200 will be described later.

(Communication Unit)

The communication unit 210 is a communication section that the information processing device 20 has, and performs various types of communication with external devices in a wireless or a wired manner via a network (or directly). For example, the communication unit 210 performs communication with the imaging device 10. More specifically, the communication unit 210 acquires a dynamic image generated by the imaging device 10. In addition, the communication unit 210 may perform communication with devices other than the imaging device 10. For example, the communication unit 210 may transmit information related to an analysis result obtained from the analysis unit 204 to be described later, information related to display of an analysis result obtained from the display control unit 205, or the like to an external information processing device, a display device, or the like.

(Storage Unit)

The storage unit 220 is a storage device installed in the information processing device 20 and stores information acquired by the communication unit 210, information obtained by the respective function units of the control unit 200, and the like. Further, the storage unit 220 appropriately outputs the stored information in response to a request from each function unit of the control unit 200 or from the communication unit 210.

Next, the functions of the respective function units installed in the control unit 200 will be described.

(Setting Unit)

The setting unit 201 sets at least one region of interest from one captured image constituting a dynamic image that the communication unit 210 acquires from the imaging device 10. Note that a region of interest refers to a region used to estimate a motion of an observation object in the present specification. This region of interest may not necessarily coincide with a region corresponding to an observation object (for example, a biological sample such as a cell) in a dynamic image (which will be referred to hereinafter as an observation object region). For example, the region of interest according to the present embodiment is described as being set in a region formed by a closed curve corresponding to a contour of the observation object, but the region of interest may be set in a region corresponding to tissue inside the observation object.

Further, the region of interest according to the present embodiment is described as being a region surrounded by a closed curve (a curve in which a starting point coincides with an ending point), but the region of interest may be a region indicated by an open curve (including a straight line). Further, a plurality of regions may be set as the region of interest, or a region indicated by a shape such as a FIG. 8 may be set.

In addition, a region of interest may be set through an operation of a user using the information processing device 20, or automatically detected from a dynamic image by the setting unit 201 using a technique such as image analysis. In the case of the latter, the setting unit 201 may detect an observation object region through image analysis. For example, the setting unit 201 may set a region of interest according to a type of observation object.

In addition, the setting unit 201 may set one or a plurality of regions of interest from one captured image. For example, when a plurality of observation objects are included in one captured image, the setting unit 201 may set regions of interest for the respective observation objects for comparison of motions of these observation objects. Accordingly, the respective motions of the plurality of observation objects can be estimated and each strain can be analyzed, and therefore the results of the analysis can be compared.

Note that the one captured image may be a captured image equivalent to a first frame of a dynamic image that the communication unit 210 acquires. By setting a region of interest for the captured image of the first frame, the position of the region of interest in the first frame can be a reference when, for example, motions of a region of interest are analyzed in a dynamic image in a time series manner. Thus, the result of the analysis becomes more accurate than when a position of a region of interest of an arbitrary captured image is set as a reference. Further, a captured image may be a captured image in a frame corresponding to a start point of analysis of the strain of the observation object by the analysis unit 204 to be described later. Accordingly, it is possible to detect the motion on the basis of a reference form of the observation object by the detection unit 203 to be described later.

In addition, when a region of interest is set in one captured image, the setting unit 201 according to the present embodiment may dispose a plurality of tracking points for the region of interest. A tracking point mentioned in the present specification is a point disposed to correspond to a region of interest set in a given captured image. In the present embodiment, for example, tracking points are disposed on a line or a contour defining a region of interest with predetermined intervals. The detection unit 203 to be described below detects positions of the tracking points in another captured image captured at a different time point from the captured image used when the region of interest is set. The detection unit 203 can detect a motion of the region of interest based on movement positions of these tracking points.

In addition, the number of tracking points disposed and disposition intervals thereof may be decided according to the type of observation object or the shape of a region of interest. For example, when the shape of the region of interest significantly changes, it is desirable to increase the number of the tracking points disposed and reduce their disposition intervals. Accordingly, even if the form of a cell significantly changes, the change in the form of the cell can be tracked with high accuracy. In addition, in order to reduce a load of calculation, it is desirable to reduce the number of the tracking points disposed and increase their disposition intervals.

Figure 4:
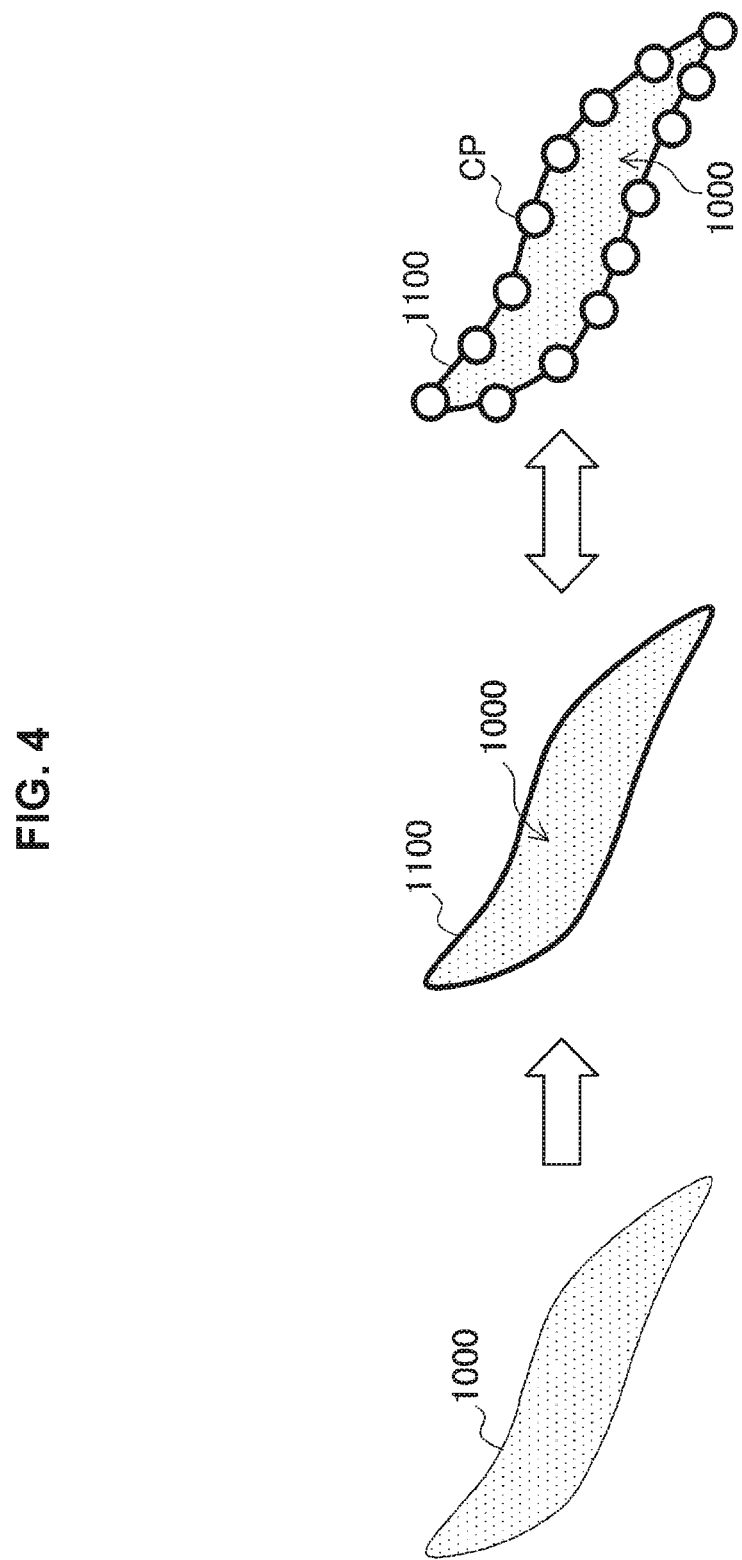
FIG. 4 is a diagram illustrating an example of a region-of-interest setting method and a tracking point arrangement method of an observation object performed by a setting unit.

Here, a region-of-interest setting method and a tracking point arrangement method performed by the setting unit 201 according to the present embodiment will be described. FIG. 4 is a diagram illustrating an example of a region-of-interest setting method and a tracking point arrangement method for the observation object performed by the setting unit 201. Referring to FIG. 4, an observation object region 1000 corresponding to an image of an observation object is assumed to be included in a captured image. In this case, as illustrated in FIG. 4, the setting unit 201 may set the observation object region 1000 as a region of interest 1100. In this case, a contour line of the region of interest 1100 may be a contour line of the observation object region 1000 (that is, a boundary line between the observation object region 1000 and a non-observation object region). Then, the setting unit 201 may arrange a plurality of tracking points CP on the contour line of the observation object region 1000 (that is, the contour line of the region of interest 1100).

Further, the region of interest 1100 illustrated in FIG. 4 may be, for example, a region corresponding to a part of the tissue or the like included in the observation object. More specifically, in a case in which a beat of a part of the tissue included in the observation object is considered to contribute to the dynamic characteristic related to the contraction and relaxation of the observation object, the setting unit 201 may set a region corresponding to a part of the tissue as the region of interest. Accordingly, it is possible to detect the dynamic characteristic of the tissue corresponding to a desired region, and it is possible to suppress a computational cost by reducing the setting size of the region of interest to the minimum necessary.

Information related to the region of interest set by the setting unit 201 is output to the analysis object specifying unit 202 and the detection unit 203.

(Analysis Object Specifying Unit)

The analysis object specifying unit 202 specifies an analysis object for at least one region of interest. The analysis object is used when the analysis unit 204 to be described later analyzes the strain. The analysis object may be decided in accordance with selection of the user or in accordance with a type of strain (for example, the macro strain or the micro strain) analyzed by the analysis unit 204 or the like.

For example, the analysis object according to the present embodiment is (1) two measurement points arranged on the contour line of the region of interest or (2) the inside of the region of interest. The analysis object specifying unit 202 specifies either or both of the above (1) and (2) as the analysis object. A method by which the analysis object specifying unit 202 specifies the analysis object related to the above (1) and (2) will be described below.

(1) Method of Specifying Two Measurement Points

The analysis object specifying unit 202 may arrange two measurement points on the contour line of the region of interest as the analysis object. The two measurement points are used to analyze the strain indicating the dynamic characteristic related to the contraction or relaxation of the entire observation object, that is, the macro strain. Therefore, the two measurement points can be arranged at positions corresponding to a portion of the contour line of the region of interest in which the motion is largest in the observation object when the observation object contracts or relaxes. The arrangement positions of the two measurement points are considered to be (a) a position at which the two points are arranged as far apart as possible on the contour line of the region of interest or (b) a position on the contour line of the region of interest at which the motion of the two points is largest. Regarding the above (a), for example, the analysis object specifying unit 202 may specify the arrangement position of the measurement point on the basis of the shape of the contour line of the region of interest. Further, regarding the above (b), for example, the analysis object specifying unit 202 may specify the arrangement position of the measurement point on the basis of a change in a dynamic image of the contour line of the region of interest (that is, a change in the shape of the region of interest). A specific example of the method by which the analysis object specifying unit 202 specifies the arrangement position of the measurement point will be described below.

Figure 5:
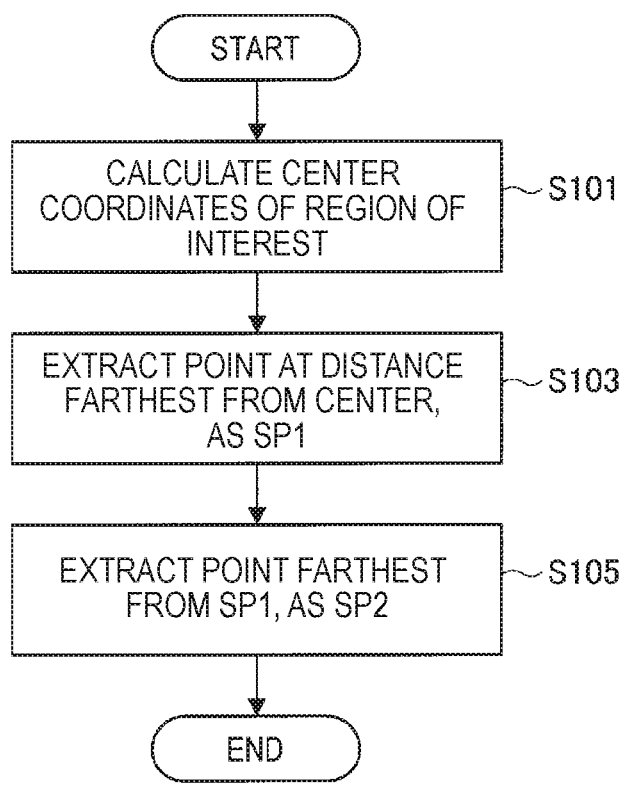
FIG. 5 is a flowchart illustrating a first example of a method by which an analysis object specifying unit specifies an arrangement position of a measurement point.

First, a method by which the analysis object specifying unit 202 specifies the arrangement position of the measurement point in the case of the above (a) will be described. FIG. 5 is a flowchart illustrating a first example of the method by which the analysis object specifying unit 202 specifies the arrangement position of the measurement point.

Figure 6:
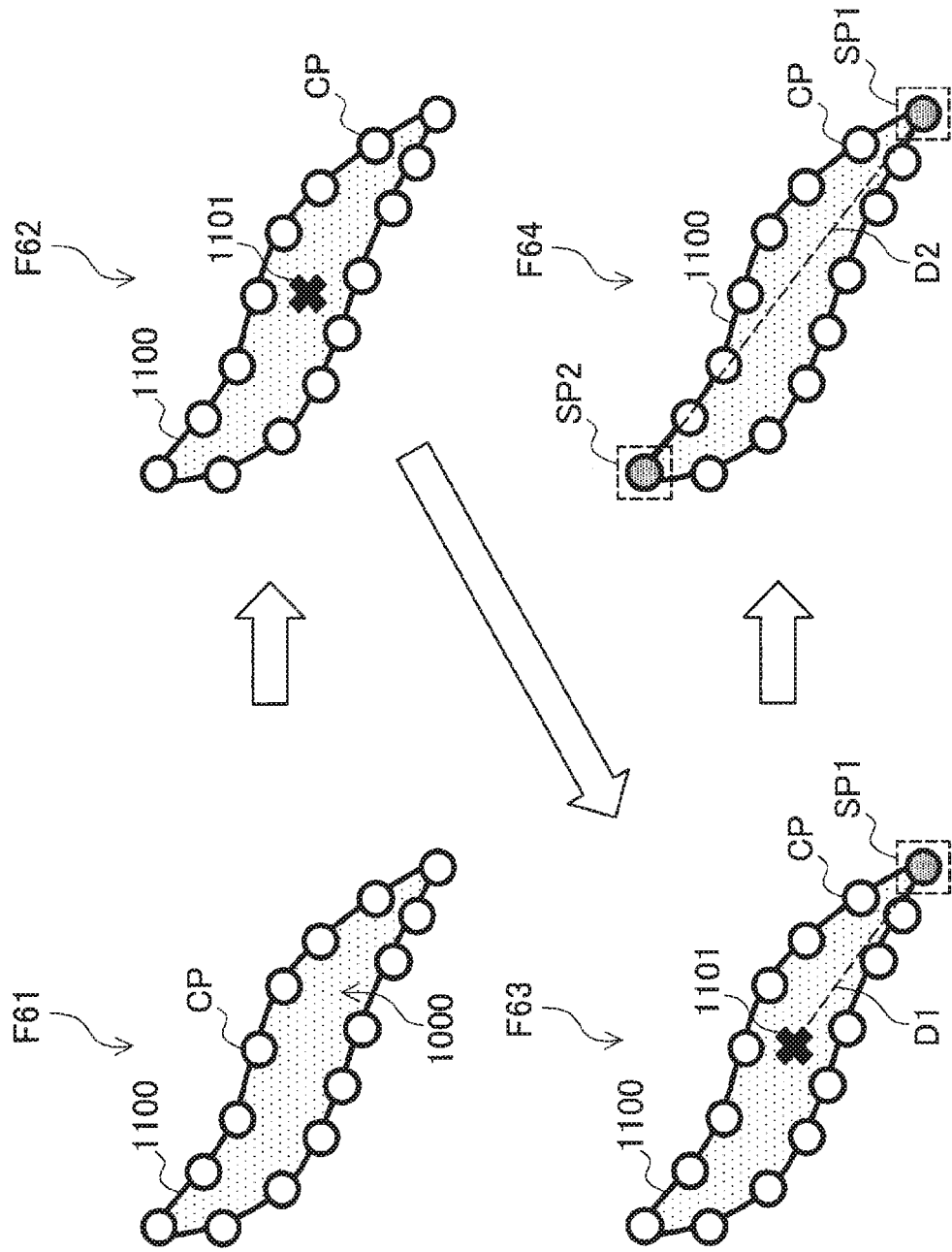
FIG. 6 is a diagram for describing a first example of a method by which an analysis object specifying unit specifies an arrangement position of a measurement point.

Further, FIG. 6 is a diagram for describing the first example of the method by which the analysis object specifying unit 202 specifies the arrangement position of the measurement point. First, the analysis object specifying unit 202 calculates center coordinates of the region of interest (S101 in FIG. 5). For example, in a case in which the region of interest 1100 and a plurality of tracking points CP are arranged for the observation object as illustrated in a schematic diagram F61 of FIG. 6, the analysis object specifying unit 202 calculates coordinates of a center point 1101 of the region of interest 1100 (see a schematic diagram F62 in FIG. 6). The center point 1101 may be calculated, for example, as a weighted average of the coordinates of a plurality of tracking points CP arranged in the region of interest 1100. Further, the center point 1101 may be calculated using a known method of obtaining the center coordinates.

Then, the analysis object specifying unit 202 specifies a position of a point farthest from the center point 1101 on the contour line of the region of interest 1100 as an arrangement position of a first measurement point SP1 (S103 in FIG. 5). For example, as illustrated in a schematic diagram F63 in FIG. 6, the analysis object specifying unit 202 may specify a position of a point at which a distance D1 from the center point 1101 on the contour line of the region of interest 1100 is largest as the arrangement position of the first measurement point SP1 which is the analysis object. Further, the analysis object specifying unit 202 may specify a point farthest from the center point 1101 among arbitrary positions on the contour line of the region of interest 1100 as the first measurement point SP1 or may specify the tracking point CP farthest from the center point 1101 among the tracking points CP arranged on the contour line as the first measurement point SP1 as illustrated in a schematic diagram F63 of FIG. 6.

Then, the analysis object specifying unit 202 specifies a position of the point farthest from the first measurement point SP1 on the contour line of the region of interest 1100 as an arrangement position of a second measurement point SP2 (S105 in FIG. 5). For example, as illustrated in a schematic diagram F64 of FIG. 6, the analysis object specifying unit 202 may specify a position of the point at which a distance D2 from the first measurement point SP1 on the contour line of the region of interest 1100 is largest as the arrangement position of the second measurement point SP2 which is the analysis object. Further, the analysis object specifying unit 202 may specify a point farthest from the first measurement point SP1 among arbitrary positions on the contour line of the region of interest 1100 as the second measurement point SP2 or may specify the tracking point CP farthest from the first measurement point SP1 among the tracking points CP arranged on the contour line as the second measurement point SP2 as illustrated in a schematic diagram F64 of FIG. 6.

In general, the motion related to the contraction and relaxation of the observation object related to the region of interest often occurs in a longitudinal direction of the observation object. Therefore, it is possible to specify the measurement point on the basis of the center position in the shape of the contour line of the region of interest and analyze a motion of a portion which is largest in the motion of the observation object. Therefore, it is possible to analyze the macro strain of the observation object related to the region of interest with a high degree of accuracy. Further, in the example illustrated in FIGS. 5 and 6, the measurement point is specified on the basis of the center position of the region of interest, but the present technology is not limited to this example. For example, the analysis object specifying unit 202 may estimate two points at which a distance between two points among arbitrary two points on the contour line of the region of interest is largest from the shape of the contour line and specify the estimated two points as the measurement point.

Figure 7:
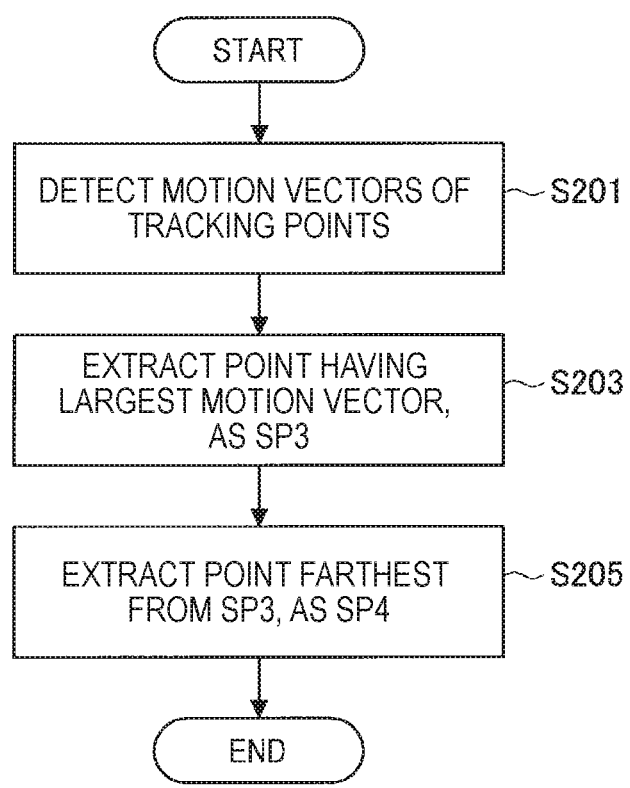
FIG. 7 is a flowchart illustrating a second example of a method by which an analysis object specifying unit specifies an arrangement position of a measurement point.
Figure 8:
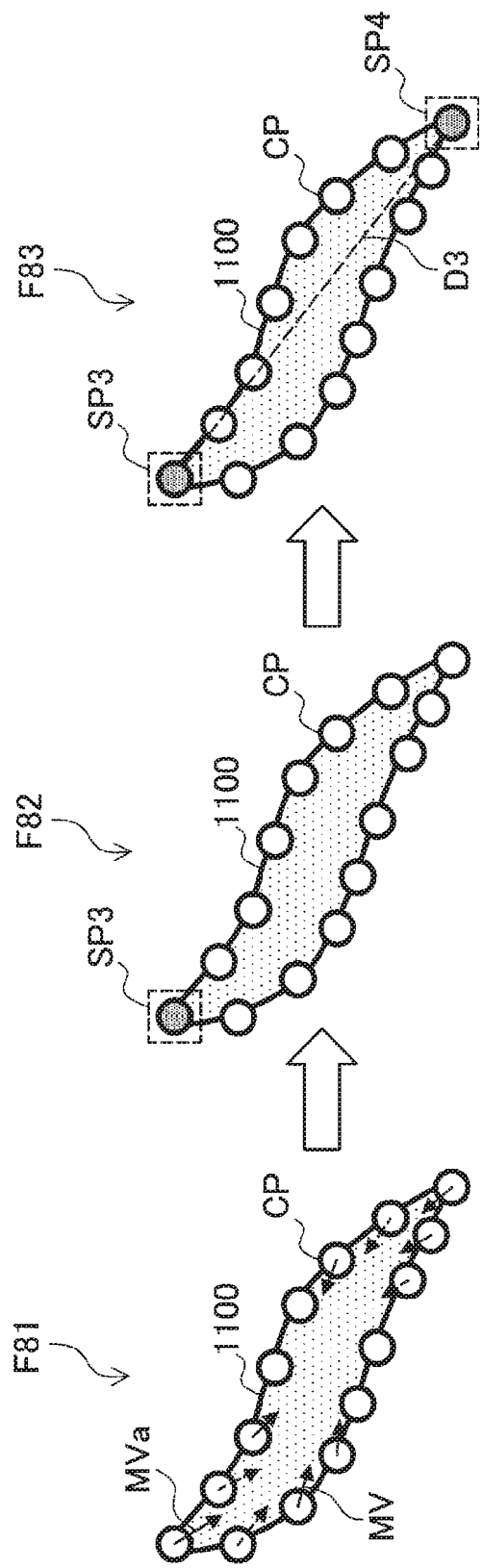
FIG. 8 is a diagram for describing a second example of a method by which an analysis object specifying unit specifies an arrangement position of a measurement point.

Next, a method by which the analysis object specifying unit 202 specifies the arrangement position of the measurement point in the case of the above (b) will be described. FIG. 7 is a flowchart illustrating a second example of the method by which the analysis object specifying unit 202 specifies the arrangement position of the measurement point. Further, FIG. 8 is a diagram for describing the second example of the method by which the analysis object specifying unit 202 specifies the arrangement position of the measurement point. First, before the analysis object specifying process by the analysis object specifying unit 202, the detection unit 203 detects a motion vector of the tracking point arranged on the contour line of the region of interest (S201 in FIG. 7). For example, in a case in which the region of interest 1100 and a plurality of tracking points CP are arranged for the observation object as illustrated in a schematic diagram F81 in FIG. 8, the detection unit 203 calculates a motion vector MV of each tracking point CP. Further, the method of calculating the motion vector MV will be described later. Further, a motion to be detected here is the motion vector MV calculated on the basis of the motion at two consecutive times when the observation object contracts or relaxes, but the present technology is not limited to this example. For example, a motion to be detected may be a displacement amount calculated on the basis of the magnitude of the motion of each tracking point CP when one period of contraction and relaxation is performed. Here, as will be described in detail later, the detection unit 203 may rearrange the tracking point at an appropriate position for the region of interest after the movement. In this case, there is a possibility that the position of the tracking point CP is changed appropriately. Therefore, in a case in which the measurement point is set on the basis of the displacement amount related to the tracking point CP, the rearrangement of the tracking point CP by the detection unit 203 may not be performed.

Then, the analysis object specifying unit 202 specifies the tracking point CP having the largest detected motion among the detected tracking points CP as a first measurement point SP3 (S203 in FIG. 7). For example, as illustrated in a schematic diagram F81 of FIG. 8, the analysis object specifying unit 202 may specify the tracking point CP indicating the largest motion vector MVa among the motion vectors MV calculated by the detection unit 203 as the first measurement point SP3 (see a schematic diagram F82 of FIG. 8).

Then, the analysis object specifying unit 202 specifies a position of the point farthest away from the first measurement point SP3 on the contour line of the region of interest 1100 as an arrangement position of a second measurement point SP4 (S205 in FIG. 7). For example, as illustrated in a schematic diagram F83 of FIG. 8, the analysis object specifying unit 202 may specify a position of a point at which a distance D3 from the first measurement point SP3 on the contour line of the region of interest 1100 is largest as the arrangement position of the second measurement point SP4 which is the analysis object. Further, the analysis object specifying unit 202 may specify a point farthest from the first measurement point SP3 among arbitrary positions on the contour line of the region of interest 1100 as the second measurement point SP4 or may specify the tracking point CP farthest from the first measurement point SP3 among the tracking points CP arranged on the contour line as the second measurement point SP4 as illustrated in a schematic diagram F83 of FIG. 8.

As described above, it is possible to specify the position which is largest in motion in the contour line of the region of interest as the measurement point and analyze a motion of a portion which is largest in the motion of the observation object. Therefore, it is possible to analyze the macro strain of the observation object related to the region of interest with a high degree of accuracy.

Further, it is preferable that the measurement point specified once be fixed in a period in which it is a strain analysis object. This is to consecutively measure the motion of the measurement point through single analysis.

Further, the tracking region of the specified measurement point (the region centered on the measurement point which is taken into account in the detection of the motion of the measurement point by the detection unit 203 to be described later) is set to a predetermined size.

(2) Specifying Method in Case in which Inside of Region of Interest is Analysis Object Further, the analysis object specifying unit 202 may specify the inside of the region of interest as the analysis object. At this time, for example, the analysis object specifying unit 202 performs a segmentation process on a captured image using the region of interest in order to detect the motion inside the region of interest specified as the analysis object. The segmentation process is a process of extracting an image of a portion corresponding to the region of interest from the captured image.

Figure 9:
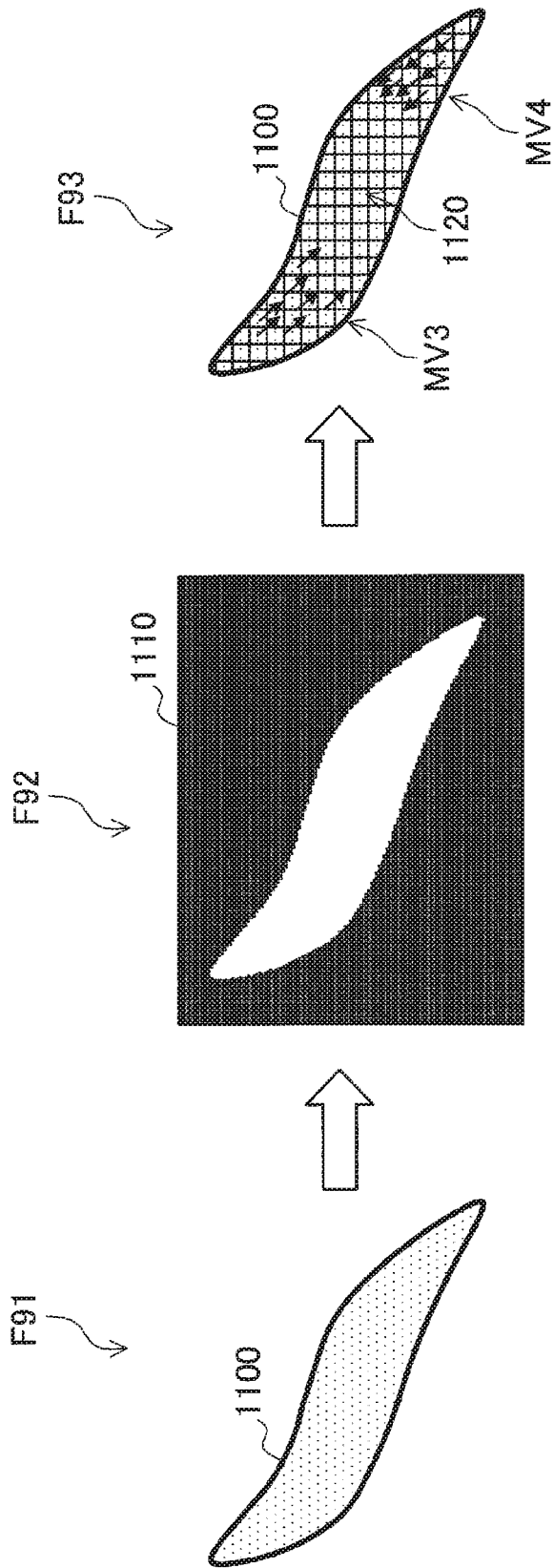
FIG. 9 is a diagram for describing an example of a method by which an analysis object specifying unit specifies an analysis object by an analysis object specifying unit.

FIG. 9 is a diagram for describing an example of the method of specifying the analysis object by the analysis object specifying unit 202. Referring to a schematic diagram F91 and a schematic diagram F92 of FIG. 9, the analysis object specifying unit 202 generates a mask 1110 with the region of interest 1100 set for the observation object region 1000 as a closed region. The segmentation process is performed by applying the mask 1110 to the captured image for the observation object region 1000.

Then, the analysis object specifying unit 202 cuts a mesh 1120 inside the region of interest 1100 after the segmentation process (a mesh processing. See a schematic diagram F93 of FIG. 9). Motion vectors MV3 and MV4 detected for the respective meshes 1120 are detected by the detection unit 203 as the motion of the analysis object. In other words, the motion inside the region of interest in the present embodiment corresponds to a motion of each mesh.

Further, the region of interest moves or is deformed depending on the change in the form of the observation object. In other words, the generated mask 1110 may be generated by the analysis object specifying unit 202 for each movement or deformation of the region of interest (for example, for each captured image). In other words, the segmentation process is performed on the region of interest in which the motion detection result detected by the detection unit 203 to be described later is reflected. The segmentation process related to the generation of the mask 1110 is not performed on the basis of the image recognition of the observation object included in the captured image but performed on the basis of the process of detecting the motion of the region of interest. Therefore, since a processing load related to the image recognition does not occur, the computational cost can be suppressed.

Further, the analysis object specifying unit 202 may specify only a part of the inside of the region of interest as the analysis object. For example, the analysis object specifying unit 202 may specify only a region corresponding to a part of the region of interest in which the change in the form of the corresponding observation object is large in the inside of the region of interest as the analysis object. Accordingly, since the motion detection process is not performed on a part with a relatively small change in form, the computational cost is suppressed.

The analysis object specified by the analysis object specifying unit 202 may be both the two measurement points and the inside of the region of interest. By specifying a plurality of analysis objects, it becomes possible to comprehensively evaluate the strains for the observation objects using the results of the macro strains and the micro strains.

The analysis object specifying unit 202 outputs information related to the specified analysis object to the detection unit 203.

(Detection Unit)

The detection unit 203 detects at least motion of the analysis object in the dynamic image specified by the analysis object specifying unit 202. Further, the detection unit 203 may detect the motion of the region of interest in the dynamic image. As illustrated in FIG. 3, the detection unit 203 includes a region-of-interest motion detection unit 231 and an analysis object motion detection unit 232.

—Region-of-interest Motion Detection Unit

The region-of-interest motion detection unit 231 has a function of detecting the motion of region of interest. For example, the region-of-interest motion detection unit 231 detects the motion of the region of interest in another captured image having a different capturing time point from one captured image constituting the dynamic image in one captured image. More specifically, the region-of-interest motion detection unit 231 first detects the motions of the respective tracking points arranged for the region of interest, and detects the motion of region of interest on the basis of the estimated motions of respective tracking points.

First, the region-of-interest motion detection unit 231 according to the present embodiment detects the motions of the tracking points disposed for the region of interest set by the setting unit 220, and thereby estimates the motion of the region of interest. Specifically, the region-of-interest motion detection unit 231, at first, estimates positions of the tracking points that have been disposed in one captured image in another captured image of which the capturing time point is different from the one captured image. The other captured image may be a captured image of any frame among a few frames before and after the frame of the one captured image. The region-of-interest motion detection unit 231 detects the motions of the tracking points in the dynamic image by performing a process for estimating positions of the tracking points in another captured image for respective captured images constituting the dynamic image. Further, the motion detected by the region-of-interest motion detection unit 231 may be a motion in the entire dynamic image or a part of the dynamic image.

The region-of-interest motion detection unit 231 may estimate positions of the tracking points based on, for example, a motion vector calculated by comparing a captured image to another captured image. This motion vector may be a motion vector calculated for each tracking point. The motion vector may be calculated using a technique such as block matching, or a gradient method. The region-of-interest motion detection unit 231 according to the present embodiment is described as estimating the motion vector using block matching.

For example, with regard to a tracking region in a predetermined size including tracking points, the region-of-interest motion detection unit 231 may estimate positions of the tracking points in the other captured image by detecting a region of which information of pixels included in the tracking region of the captured image matches that of the other captured image from a predetermined block size (search range) of the other captured image. In this case, a size of the tracking region and the block size may be decided according to an imaging condition (for example, an imaging magnification) of the imaging device 10, the type of the observation object, the type of analysis performed on the observation object. When a movement of the observation object is large, for example, the tracking region or the block size may be set to be larger. Accordingly, accuracy in estimation of tracking points by the region-of-interest motion detection unit 231 can be enhanced. In addition, when there are a number of tracking points for a region of interest, the tracking region or the block size may be adjusted to be small in order to reduce a load of calculation.

In addition, the region-of-interest motion detection unit 231 may estimate a position of a tracking point in the other captured image generated at an imaging time point decided based on information of the observation object. When a change in the morphology of an observation object of which a speed of the change in the morphology is slow is tracked, for example, a difference in captured images between a plurality of consecutive frames generated by the imaging device 10 is small. For this reason, when a change in the shape of an observation object of which a speed of the change in the shape is slow is tracked, the region-of-interest motion detection unit 231 may perform a detection process with a captured image a number of frames before or after the frame of the captured image as the other captured image. To be more specific, the region-of-interest motion detection unit 231 may perform a detection process with a captured image a number frames after the captured image as the other captured image. The frame interval between the captured image and the other captured image enables the data amount of the captured image that is subject to a tracking process to be reduced. Accordingly, it is possible to reduce a load of calculation and track a motion of the region of interest over a long period of time. The frame interval can be appropriately set according to the type, a state, or the like of the observation object.

The region-of-interest motion detection unit 231 further detects the motion of the region of interest (for example, the movement of region of interest or the change in the shape of the contour line of the region of interest) on the basis of the movement positions of the detected tracking points. Accordingly, it is possible to track the change in the form of the observation object related to the region of interest. Further, the region-of-interest motion detection unit 231 may rearrange the tracking points for the region of interest after the motion detection. Accordingly, the estimation accuracy of the motion of the region of interest can be improved.

The information related to the motion of the region of interest may be output to the analysis object specifying unit 202. Accordingly, in a case in which the analysis object specifying unit 202 specifies the inside of the region of interest as the analysis object, the segmentation process can be performed in accordance with the motion of the region of interest.

—Analysis Object Motion Detection Unit

The analysis object motion detection unit 232 has a function of detecting the motion of the analysis object. For example, the analysis object motion detection unit 232 detects the motion of the analysis object in another captured image having a different capturing time point from one captured image constituting the dynamic image in one captured image. More specifically, the analysis object motion detection unit 232 may estimate the motion of the analysis object on the basis of the motion vector calculated by comparing one captured image with another captured image. The detected motion vector is implemented by a method similar to the method performed by the region-of-interest motion detection unit 231 such as block matching. The analysis object motion detection unit 232 according to the present embodiment is assumed to detect the motion vector of the analysis object through the block matching. Further, the motion detected by the analysis object motion detection unit 232 may be a motion in the entire dynamic image or a part of the dynamic image.

For example, in a case in which the measurement point is arranged on the contour line of the region of interest by the analysis object specifying unit 202, the analysis object motion detection unit 232 detects the motion vector of the measurement point in the dynamic image. Further, in a case in which the analysis object specifying unit 202 specifies the inside of the region of interest as the analysis object, the analysis object motion detection unit 232 detects the motion vectors of the respective meshes included in the region of interest.

Further, in the present embodiment, a detector used in the region-of-interest motion detection unit 231 may be different from a detector used in the analysis object motion detection unit 232. For example, in a case in which the detector for detecting the motion vector by the block matching is used in the region-of-interest motion detection unit 231 and the analysis object motion detection unit 232, the block size may be different between the region-of-interest motion detection unit 231 and the analysis object motion detection unit 232.

Figure 10:
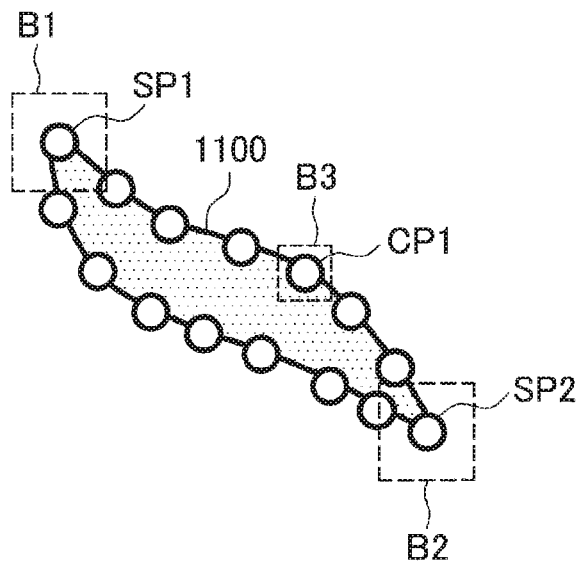
FIG. 10 is a diagram illustrating an example of a block size used in a region-of-interest motion detection unit and a block size used in an analysis object motion detection unit.
Figure 11:
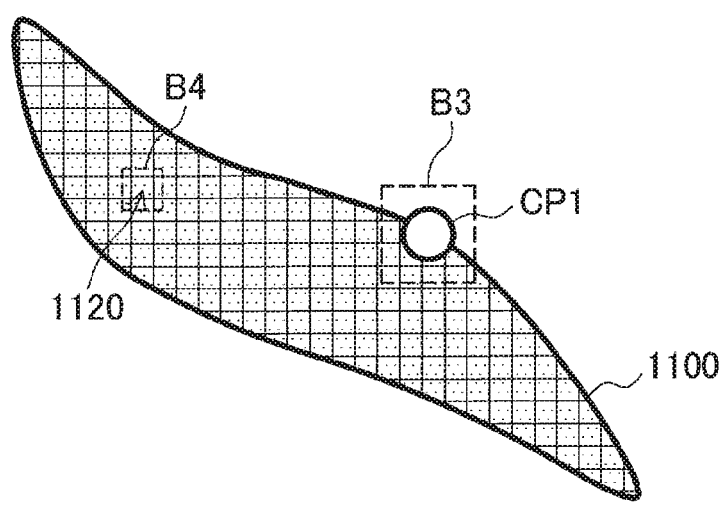
FIG. 11 is a diagram illustrating an example of a block size used in a region-of-interest motion detection unit and a block size used in an analysis object motion detection unit.

FIGS. 10 and 11 are diagrams illustrating examples of a block size used in the region-of-interest motion detection unit 231 and a block size used in the analysis object motion detection unit 232. FIG. 10 illustrates an example in which the measurement point is arranged on the contour line of the region of interest as the analysis object, and FIG. 11 illustrates an example in which the inside of the region of interest is specified as the analysis object.

As illustrated in FIG. 10, for example, block sizes B1 and B2 of the measurement points SP1 and SP2 may be equal to or larger than a block size B3 of the tracking point CP1. The measurement points SP1 and SP2 are larger in a change in position than the other tracking points CP. Therefore, the block sizes of the measurement points SP1 and SP2 may be set to be equal to or larger than the block size of the tracking point CP in order to more reliably detect the change in shape caused by the contraction or relaxation of the observation object.

Further, as illustrated in FIG. 11, for example, a block size B4 of the mesh 1120 may be equal to or smaller than the block size B3 of the tracking point CP1. In a case in which the block size B4 is set to be too large, there is a possibility that an image pattern close to an image pattern included in the mesh 1120 before the motion detection is detected in a portion other than a portion near the mesh 1120.

Further, the sizes of the block sizes may be appropriately changed in accordance with a type of captured image (a bright field image, a phase difference image, or the like) for the observation object.

Further, in the above example, the block size is assumed to be different between the region-of-interest motion detection unit 231 and the analysis object motion detection unit 232, but the present technology is not limited to this example. For example, the size of the tracking region may be different between the region-of-interest motion detection unit 231 and the analysis object motion detection unit 232.

As described above, since the different detectors are used in the region-of-interest motion detection unit 231 and the analysis object motion detection unit 232, the motion detection according to the characteristic of each motion can be performed. Accordingly, the accuracy of motion detection is improved.

The region-of-interest motion detection unit 231 detects the motion of the region of interest for each captured image constituting the dynamic image. Further, the analysis object motion detection unit 232 detects the motion of the analysis object for each captured image. Then, the analysis object motion detection unit 232 outputs the information related to the motion of the detected analysis object to the analysis unit 204. Further, the information related to the detection result of the region of interest and the motion of the analysis object by the detection unit 203 is output to the display control unit 205.

(Analysis Unit)

The analysis unit 204 analyzes the strain of the observation object related to at least one region of interest on the basis of the motion of the analysis object. The analysis unit 204 according to the present embodiment analyzes at least either the macro strain or the micro strain on the basis of the motion vector of at least one of the measurement point or the inside (mesh) of the region of interest specified by the analysis object specifying unit 202. An example of the analysis process by the analysis unit 204 will be described below.

—Macro Strain Analysis Based on Motion of Measurement Point

Figure 12:
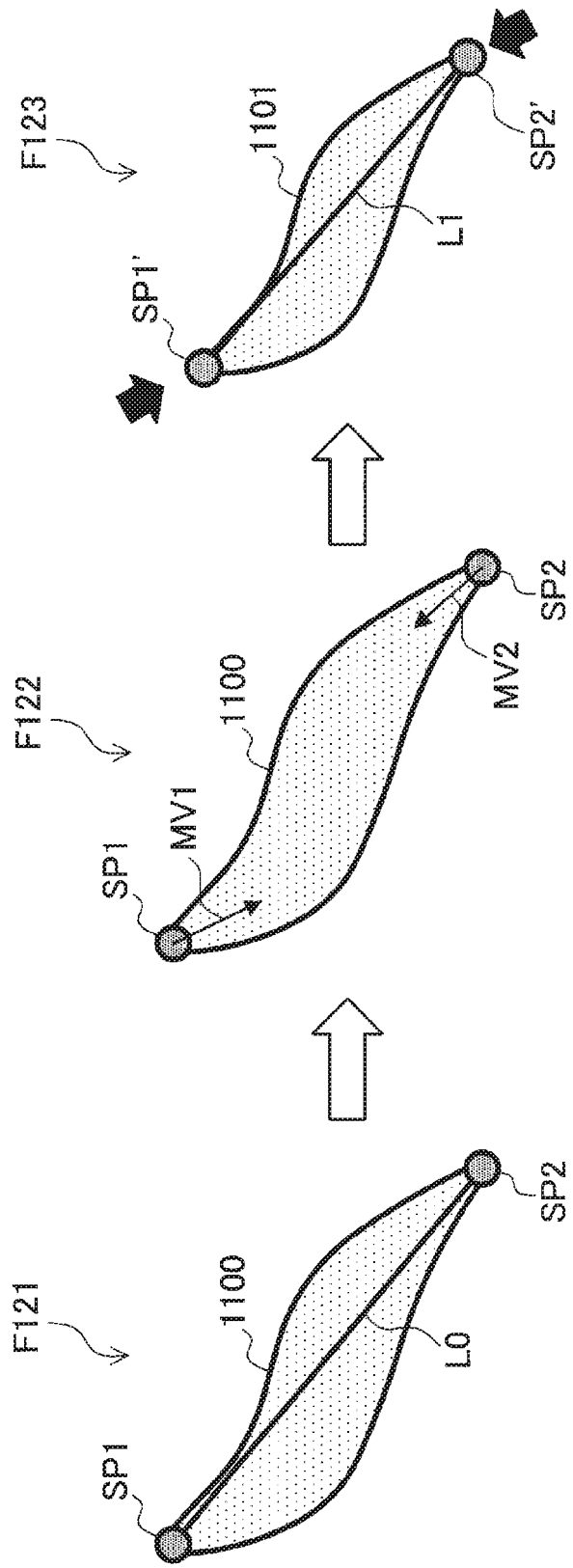
FIG. 12 is a diagram illustrating a first example of macro strain analysis based on a motion vector of a measurement point.

The analysis unit 204 may perform the macro strain analysis on the observation object on the basis of the motion vector of the measurement point specified on the contour line of the region of interest by the analysis object specifying unit 202. FIG. 12 is a diagram illustrating a first example of the macro strain analysis based on the motion vector of the measurement point. As illustrated in a schematic diagram F121 in FIG. 12, the analysis unit 204 first calculates a distance $L(t_0)$ of a line segment L0 connecting measurement points SP1 and SP2. This distance $L(t_0)$ is calculated from positions of the measurement points SP1 and SP2 in a captured image captured at a time different from a time at which the observation object contracts or relaxes.

When the observation object contracts or relaxes (contracts in a schematic diagram F122 of FIG. 12), motion vectors MV1 and MV2 of the measurement points SP1 and SP2 in the dynamic image are detected. At this time, a distance $L(t)$ of a line segment L1 connecting measurement points SP1' and SP2' is shorter than the distance $L(t_0)$ (see a schematic diagram F123 of FIG. 12). Further, the position after the movement of the measurement point is estimated on the basis of the motion vector detected by the detection unit 203 (the analysis object motion detection unit 232). In this case, a macro strain 40 is indicated by the following Formula (1).

[Math. 1]

$$\varepsilon(t) = \frac{L(t_0) - L(t)}{L(t_0)} \quad (1)$$

The analysis unit 204 analyzes the macro strain 40 over time by tracking the changes in the positions of the measurement points SP1 and SP2.

Figure 13:
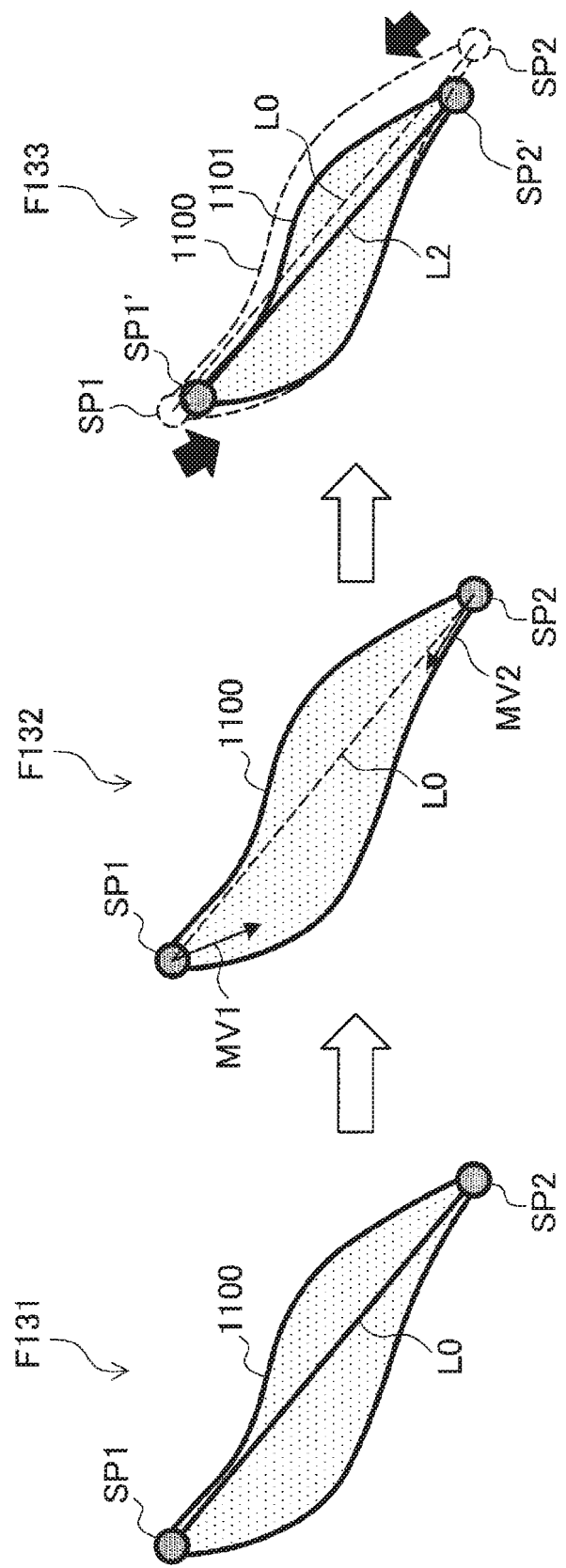
FIG. 13 is a diagram illustrating a second example of macro strain analysis based on a motion vector of a measurement point.

Further, the method of calculating the macro strain $\varepsilon(t)$ is not limited to the example illustrated in FIG. 12. FIG. 13 is a diagram illustrating a second example of the macro strain analysis based on the motion vector of the measurement point. As illustrated in a schematic diagram F131 of FIG. 13, the analysis unit 204 first calculates a distance $L(t_0)$ of a line segment L0 connecting measurement points SP1 and SP2. This distance $L(t_0)$ is calculated from positions of the measurement points SP1 and SP2 in the captured image captured at a time different from a time at which the observation object contracts or relaxes. The analysis unit 204 sets the line segment L0 as a reference line.

When the observation object contracts or relaxes., the motion vectors of the measurement points SP1 and SP2 in the dynamic image are detected (see a schematic diagram F132 of FIG. 13). If a line segment connecting the measurement points SP1' and SP2' at this time is a line segment L2 (see a schematic diagram F133 of FIG. 13), the distance $L(t)$ described above may be a length when the line segment L2 is projected onto the reference line L0. In a case in which the directions of the motion vectors MV1 and MV2 of the measurement points SP1 and SP2 are not parallel to the reference line L0, a part of force related to the contraction and relaxation of the observation object is considered to contribute the change in the direction of the reference line L0, that is, the change in the enlargement and contraction direction of the observation object. By projecting the line segment L2 onto the reference line L0, it is possible to analyze the macro strain contributing to the change in the enlargement and contraction direction of the observation object.

—Micro Strain Analysis Based on Motion of Mesh

In a case in which the analysis object specifying unit 202 specifies the inside of the region of interest as the analysis object, the analysis unit 204 may perform the micro strain analysis on the observation object on the basis of the motion vector of the inside of the region of interest. Specifically, the analysis unit 204 may analyze a time change amount (that is, acceleration) of the motion vector of each mesh as the micro strain. The micro strain to be analyzed here is a micro strain of each mesh. Accordingly, it is possible to obtain a partial strain of the observation object corresponding to the region of interest. In other words, it is possible to detect a local dynamic characteristic of the contraction and relaxation of observation object in further detail.

Further, by applying a Green-Lagrange distortion tensor to the micro strain obtained for each mesh, the strain serving as the local dynamic characteristic in the region in which the micro strain is analyzed can be obtained. Further, a statistical value such as an average value, a median value, a maximum value, or a minimum value of the micro strain obtained for each mesh can be a value indicating the local dynamic characteristic in the region in which the micro strain is analyzed.

—Strain Analysis Using Affine Parameter

Further, in a case in which the analysis object specifying unit 202 specifies the inside of the region of interest as the analysis object, the analysis unit 204 may calculate an affine parameter from the motion vector of the inside of the region of interest and analyze the strain (the macro strain or the micro strain) on the basis of the affine parameter. The affine parameter according to the present embodiment is obtained by applying a least squares technique to the motion vectors of each mesh. By using the affine parameter, it is possible to analyze both the macro strain and the micro strain.

Figure 14:
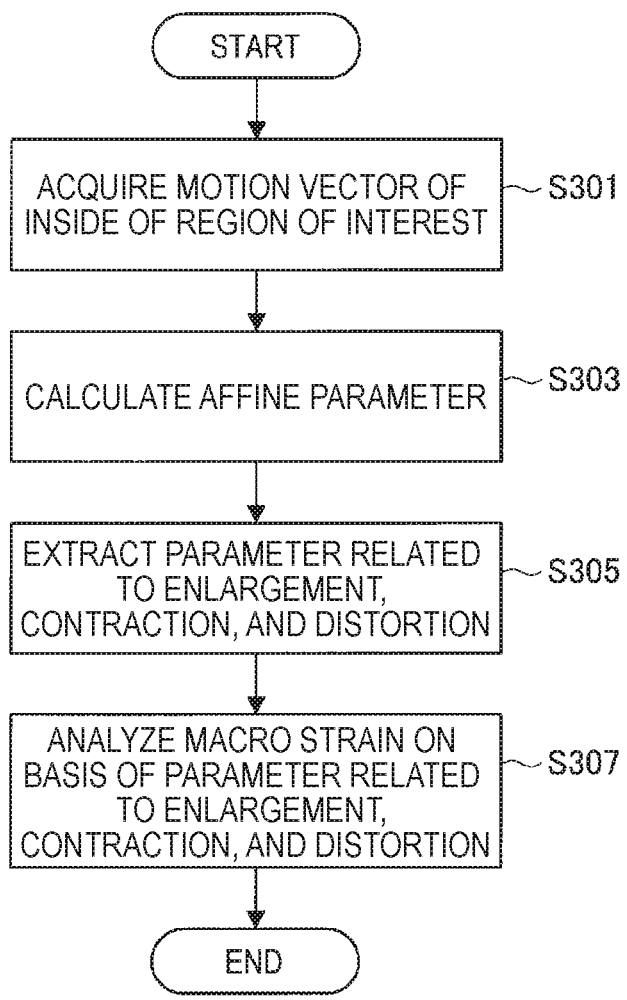
FIG. 14 illustrates an example of a flowchart illustrating a process of analyzing a macro strain using an affine parameter.

FIG. 14 is an example of a flowchart illustrating a process of analyzing the macro strain using the affine parameter. Referring to FIG. 14, first, the analysis unit 204 acquires the motion vector of the inside (each mesh) of the region of interest (S301). Then, the analysis unit 204 calculates the affine parameter for the obtained motion vector using the least squares technique (S303). Then, the analysis unit 204 extracts a parameter related to the enlargement and contraction and the distortion from the affine parameter (S305). The parameter related to the enlargement and contraction and the distortion is associated with the enlargement and contraction and the distortion of the region of interest in the longitudinal direction. In other words, the parameter is a parameter associated with the contraction and relaxation of the observation object. Then, the analysis unit 204 analyzes the macro strain of the observation object from the parameter related to the enlargement and contraction and the distortion (S307). Specifically, the analysis unit 204 calculates the time change amount of the parameter related to the enlargement and contraction and the distortion as an analysis value of the macro strain.

By obtaining the parameter related to the enlargement and contraction and the distortion of the entire region of interest, it is possible to analyze the macro strain on the basis of the motion vector of the inside of the region of interest without specifying the measurement point on the contour line of the region of interest. Accordingly, it is possible to analyze both the macro strain and the micro strain on the basis of only the motion in the region of interest.

Figure 15:
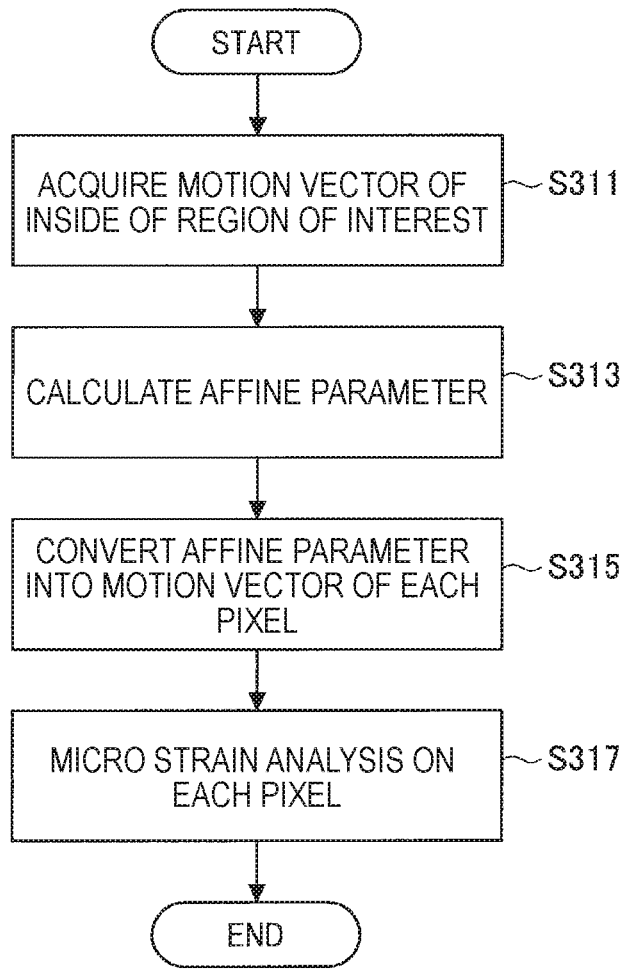
FIG. 15 illustrates an example of a flowchart illustrating a process of analyzing a micro strain using an affine parameter.

FIG. 15 is an example of a flowchart illustrating a process of analyzing the micro strain using the affine parameter. Referring to FIG. 15, first, the analysis unit 204 acquires the motion vector of the inside (each mesh) of the region of interest (S311). Then, the analysis unit 204 calculates the affine parameter for the obtained motion vector using the least squares technique (S313). Then, the analysis unit 204 converts the affine parameter into a motion vector of each pixel of the inside of the region of interest (S315). Then, the analysis unit 204 performs the micro strain analysis on each pixel on the basis of the motion vector of each pixel (S317). A micro strain analysis method is similar to the above-described micro strain analysis method of each mesh.

By converting the affine parameter into the motion vector of each pixel, it is possible to perform the micro strain analysis in finer units than meshes. Accordingly, it is possible to obtain information related to the micro strain of the observation object in further detail.

The analysis unit 204 outputs the information related to the analyzed strain to the display control unit 205.

(Display Control Unit)

The display control unit 205 controls display of the information related to the analyzed strain. For example, the display control unit 205 has a function of displaying the information related to the macro strains or micro strains analyzed for the observation object in various display forms such as a graphs, imaging, or a table. The display controlled by the display control unit 205 is displayed on a screen of a display device (not illustrated) or the like. A screen display example by the display control unit 205 will be described below.

—Graph Indicating Temporal Change in Macro Strain

Figure 16:
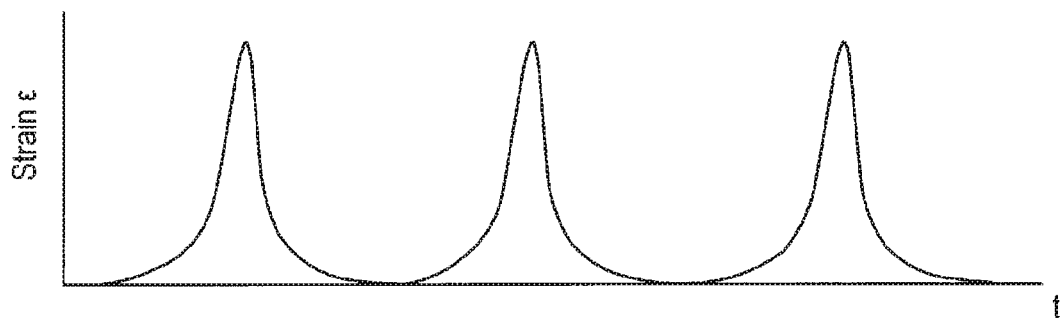
FIG. 16 illustrates an example of a graph illustrating a temporal change in a macro strain.

FIG. 16 is an example of a graph illustrating a temporal change in the macro strain. As illustrated in FIG. 16, the macro strain ε analyzed by the analysis unit 204 may be displayed as a time-series graph. By displaying the macro strain ε as the graph, it is possible to quantitatively evaluate not only the beat period of the observation object but also a characteristic of the change in the form of the observation object at the time of contraction and at the time of relaxation.

—Imaging of Contraction/relaxation

For example, the display control unit 205 may display an arrow indicating a size and a direction thereof as the micro strain. Specifically, as illustrated in FIG. 3, the arrow indicating the micro strain may be superimposed on the region of interest. Accordingly, it is possible to detect a strength and a direction in which the local distortion of the observation object by the beat occurs.

Further, the display control unit 205 may display the information related to the micro strain by imaging such as color mapping. For example, the display control unit 205 may render a portion in which the micro strain is analyzed when the observation object contracts or relaxes with a rendering color associated with the contraction state or the relaxation state of the observation object. In this case, the display control unit 205 determines whether or not the observation object is contracting or relaxing on the basis of the motion of the region of interest or the motion of the analysis object. The display control unit 205 according to the present embodiment determines whether or not the observation object is contracting or relaxing on the basis of the motions of the two measurement points.

Figure 17:
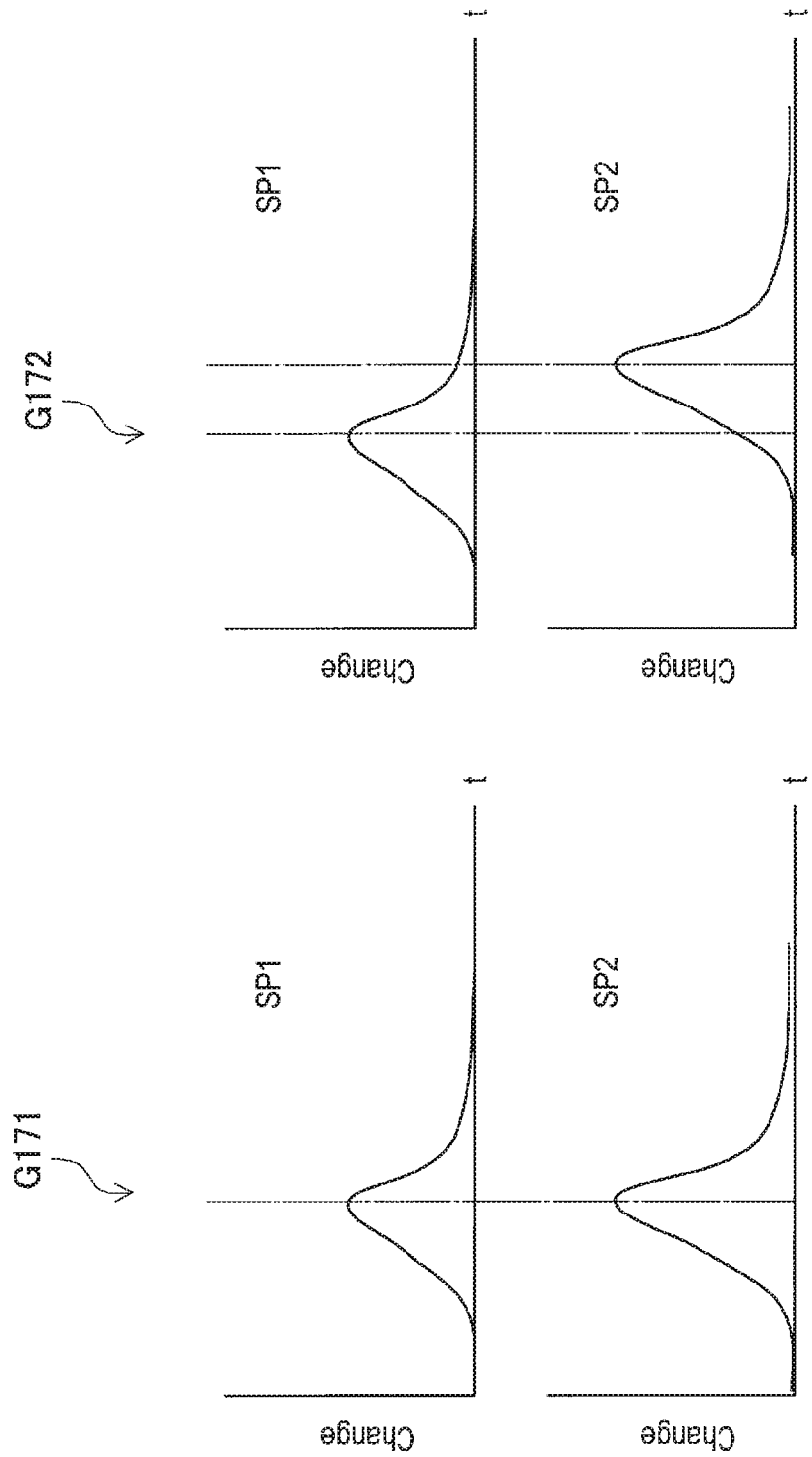
FIG. 17 is a graph illustrating an example of displacement in a case in which motions of measurement points have the same phase and in a case in which motions of measurement points have different phases.

However, motions related to contraction or relaxation of end portions of the observation object in the length direction (portions in which a motion by contraction and relaxation is largest and which corresponds to the measurement points) may have the same phase or different phases, depending on the observation object. FIG. 17 is a graph illustrating an example of displacement in a case in which the motions of the measurement points have the same phase and in a case in which the motions of the measurement points have different phases. Further, a graph related to the displacement can be obtained, for example, by integrating the motion vectors of the measurement points.

It is possible to determine whether or not the motions of the two measurement points have the same phase on the basis of peak positions of the temporal change in distances from stationary positions of the two measurement points. For example, if the measurement point SP1 and the measurement point SP2 have the same peak position, the motions of the two measurement points have the same phase (see a graph G171 of FIG. 17), and if there is a deviation between the peak positions, the motions of the two measurement points have different phases (see a graph G172 of FIG. 17).

In a case in which the motions of the two measurement points have the same phase, timings at which the observation object contracts or relaxes are totally identical. On the other hand, in a case in which the motions of the two measurement points have different phases, timings at which the observation object contracts or relaxes are different at the end portion in the longitudinal direction. In this case, for example, it is possible to estimate the position of the beat center of the observation object and determine whether a part of the observation object corresponding to each mesh is contracting or relaxing on the basis of the position of the beat center and the direction of the motion vector of each mesh. More specifically, if an inner product of a direction of the mesh to the beat center and a direction of the motion vector of each mesh is positive, it is possible to determine that the part of the observation object corresponding to each mesh is contracting. Conversely, if the inner product of the direction of the mesh to the beat center and the direction of the motion vector of each mesh is negative, it is possible to determine that the part of the observation object corresponding to each mesh is relaxing.

Further, a process related to the estimation of the beat center is implemented by a known technique. For example, the process may be implemented by a technique disclosed in JP 2014-75999 A.

Figure 18:
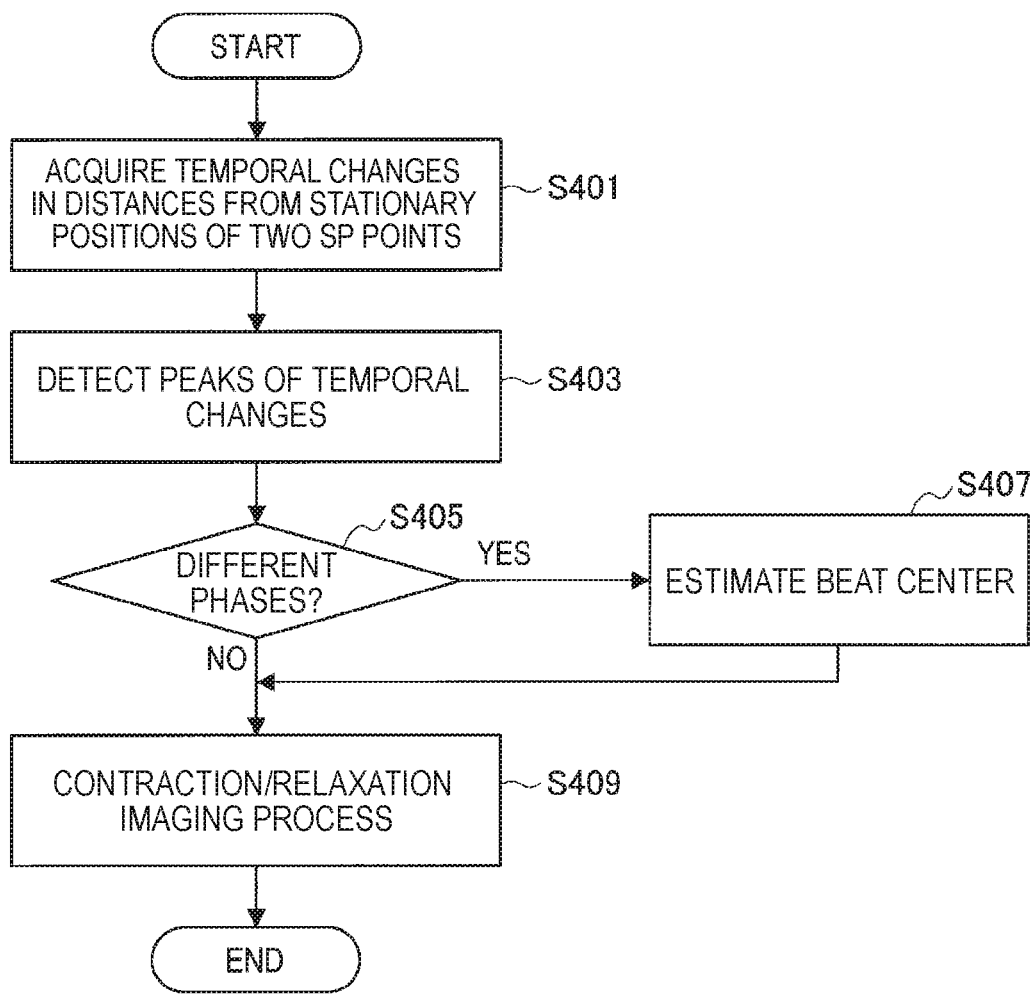
FIG. 18 illustrates an example of a flowchart of an imaging process of a micro strain related to contraction or relaxation of an observation object by a display control unit.

Next, the flow of an imaging process of the micro strain related to the contraction or relaxation of the observation object will be described. FIG. 18 illustrates an example of a flowchart of an imaging process of the micro strain related to the contraction or relaxation of the observation object by the display control unit 205. Referring to FIG. 18, first, the display control unit 205 acquires the temporal changes in the distances from the stationary positions of the two measurement points (S401). Then, the display control unit 205 detects the peak positions of the temporal changes of the two measurement points (S403). Then, the display control unit 205 determines whether the motions of the two measurement points have the same phase or different phases from the detection result of the peak positions (S405). In a case in which the motions have different phases (YES in S405), the display control unit 205 estimates the beat center of the observation object (S407).

Then, the display control unit 205 performs the imaging process on the micro strain related to the contraction or relaxation (S409). First, an imaging process in a case in which the motions of the two measurement points have the same phase will be described.

Figure 19:
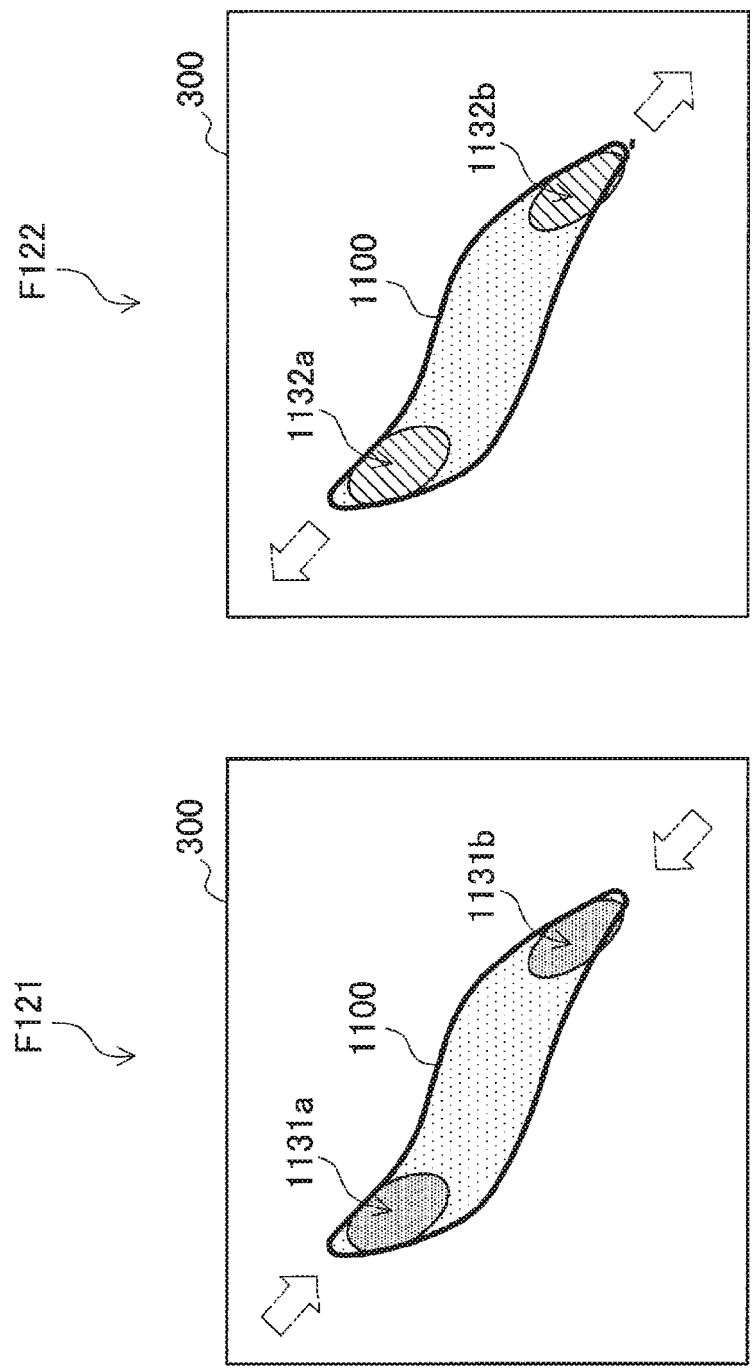
FIG. 19 is a diagram illustrating a process example of an imaging process of a micro strain related to contraction or relaxation of an observation object in a case in which motions of two measurement points have the same phase.

FIG. 19 is a diagram illustrating a process example of the imaging process of the micro strain related to the contraction or relaxation of the observation object in a case in which the motions of two measurement points have the same phase. A schematic diagram F191 of FIG. 19 is an example of the imaging process in a case in which the observation object contracts. Further, a schematic diagram F192 of FIG. 19 is an example of the imaging process in a case in which the observation object relaxes.

Referring to the schematic diagram F191, in a case in which the observation object contracts, each of the micro strains at the end portions of the region of interest 1100 indicates the contraction direction. In this case, the display control unit 205 may render regions 1131a and 1131b in which the micro strain is analyzed with a rendering color indicating the contraction, and reflect the regions 1131a and 1131b in a screen 300. Further, referring to the schematic diagram F192, in a case in which the observation object relaxes, each of the micro strains at the end portions of the region of interest 1100 may occur in the relaxation direction. In this case, the display control unit 205 may render regions 1132a and 1132b in which the micro strain is analyzed with a rendering color indicating the relaxation, and reflect the regions 1132a and 1132b in the screen 300. Since the rendering color of the region in which the micro strain is analyzed is different between when the observation object contracts and when the observation object relaxes, the user can easily determine the region indicating the dynamic characteristic contributing to the contraction or relaxation of the observation object.

Next, an imaging process in a case in which the motions of the two measurement points have different phases will be described.

Figure 20:
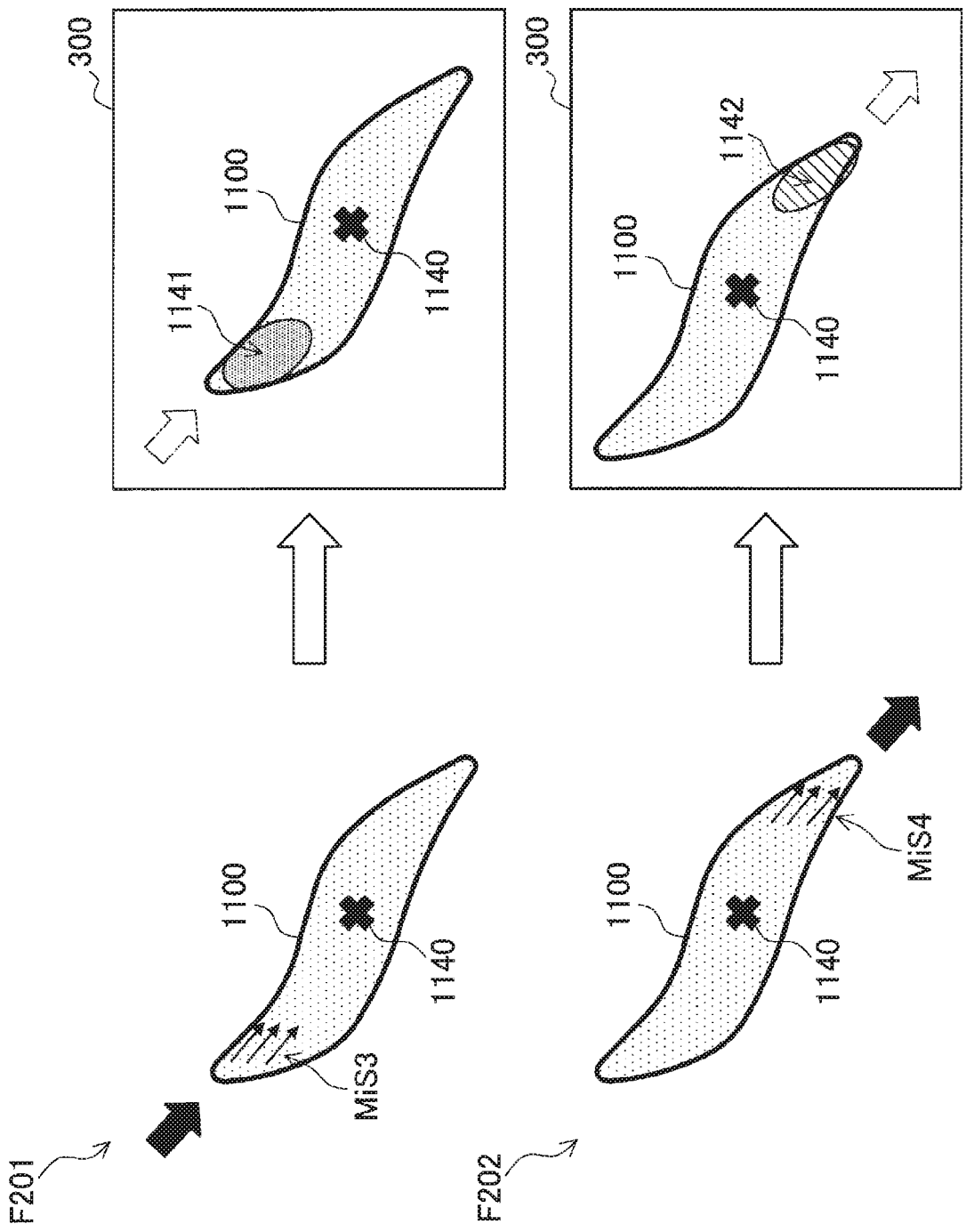
FIG. 20 is a diagram illustrating a process example of an imaging process of a micro strain related to contraction or relaxation of an observation object in a case in which motions of two measurement points have different phases.

FIG. 20 is a diagram illustrating a process example of the imaging process of the micro strain according to the contraction state or the relaxation state of the observation object in a case in which the motions of two measurement points have different phases. A schematic diagram F201 in FIG. 20 is an example of the imaging process in a case in which one end of the observation object contracts. Further, a schematic diagram F202 in FIG. 20 is an example of the imaging process in a case in which one end of the observation object relaxes.

Referring to the schematic diagram F201, a beat center 1140 is assumed to have been estimated for the region of interest 1100 in step S407 of FIG. 18. At this time, the display control unit 205 determines that a direction of an analyzed micro strain MiS3 is a direction toward the beat center 1140. In other words, the display control unit 205 determines that the micro strain MiS3 is a micro strain related to the contraction of the observation object. In this case, the display control unit 205 may render a region 1141 in which the micro strain is analyzed with a rendering color indicating the contraction and reflect the region 1141 in the screen 300.

Further, referring to a schematic diagram F202, the display control unit 205 determines that a direction of an analyzed micro strain MiS4 is a direction away from the beat center 1140. In other words, the display control unit 205 determines that the micro strain MiS4 is a micro strain related to the relaxation of the observation object. In this case, the display control unit 205 may render a region 1142 in which the micro strain is analyzed with a rendering color indicating the relaxation, and reflect the region 1142 in the screen 300.

As described above, by using the beat center, even when the motions of the end portions of the observation object have different phases, the region contributing to the contraction and relaxation of the observation object can be presented to the user. Further, the beat center 1140 illustrated in FIG. 20 may be displayed or may not be displayed on the screen 300.

Further, in a case in which the motions of the end portions of the observation object when the observation object contracts or relaxes are detected to have the same phase in advance, the determination of whether the observation object is contracting or relaxing is not limited to the example in which it is performed using the two measurement points. For example, the display control unit 205 may control the display form of the information related to the strain on the basis of the change in the shape of the contour line of the region of interest.

Specifically, it may be determined whether the observation object is contracting or relaxing on the basis of the temporal change (shape differential) in the length of the contour line of the region of interest or the area surrounded by the contour line, and the rendering of the micro strain illustrated in FIG. 19 may be controlled on the basis of the determination result. More specifically, in a case in which the length of the contour line is decreasing chronologically, the observation object is considered to be contracting. Further, in a case in which the length of the contour line is increasing chronologically, the observation object is considered to be relaxing. As described above, it is possible to determine the contraction state or the relaxation state of the observation object on the basis of the change in the shape of the contour line of the region of interest. Therefore, it is possible to control a rendering form related to the micro strain on the basis of the change in the shape of the contour line.

—Imaging of Strain Strength

Further, the display control unit 205 may control the display form of the information related the strain on the basis of the strength (size) of the micro strain. For example, the display control unit 205 may render a portion in which the micro strain is analyzed when the observation object contracts or relaxes with a rendering color associated with the strength of the micro strain.

Figure 21:
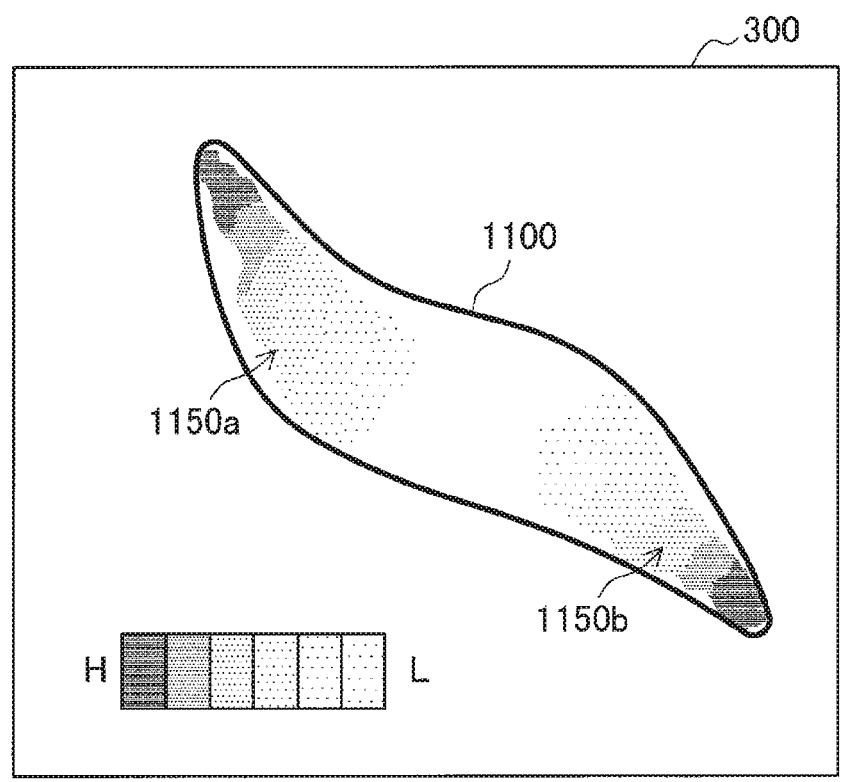
FIG. 21 is a diagram illustrating an example of an imaging process of a strain strength.

FIG. 21 is a diagram illustrating an example of the imaging process of the strain strength. Referring to FIG. 21, the display control unit 205 renders regions 1150a and 1150b in which the micro strain is analyzed with a rendering color corresponding to the size of the micro strain in the screen 300. Accordingly, it is possible to intuitively recognize the distribution of the micro strain in the region contributing to the contraction or relaxation of the observation object.

Further, in the imaging process of the micro strain according to the contraction state or the relaxation state of the observation object described above, the display control unit 205 may control a contrasting density of the rendering color associated with the contraction state or the relaxation state in accordance with the strength (size) of the micro strain. Accordingly, it is possible to obtain the strength distribution of the micro strain in the region illustrating the dynamic characteristic contributing to the contraction or relaxation of the observation object.

The display control example by the display control unit 205 has been described above. Further, the information related to the analyzed strain may be output to another display device, a storage device, or the like via the communication unit 210 or may be stored in the storage unit 220.

Further, the number of observation objects in which the strain is analyzed by the information processing device 20 according to the present embodiment is not particularly limited. For example, in a case in which images of a plurality of observation objects are included in the dynamic image, the region of interest may be set in each of a plurality of observation objects, the analysis object may be specified for each of a plurality of regions of interest, the motion of each of the specified analysis objects may be detected, and the strain of each of the observation objects may be analyzed on the basis of each motion. In this case, the strain analyzed for each observation object may be normalized. The size of the strain also differs in accordance with the size of the observation object. By normalizing the strain, it becomes possible to compare the analysis results of the strain or the like among a plurality of observation objects.

<2.2. Process Example>

The configuration and functions of the information processing device 20 according to one embodiment of the present disclosure have been described above. Next, an example of a process by the information processing device 20 according to one embodiment of the present disclosure will be described with reference to FIGS. 22 to 24.

Figure 22:
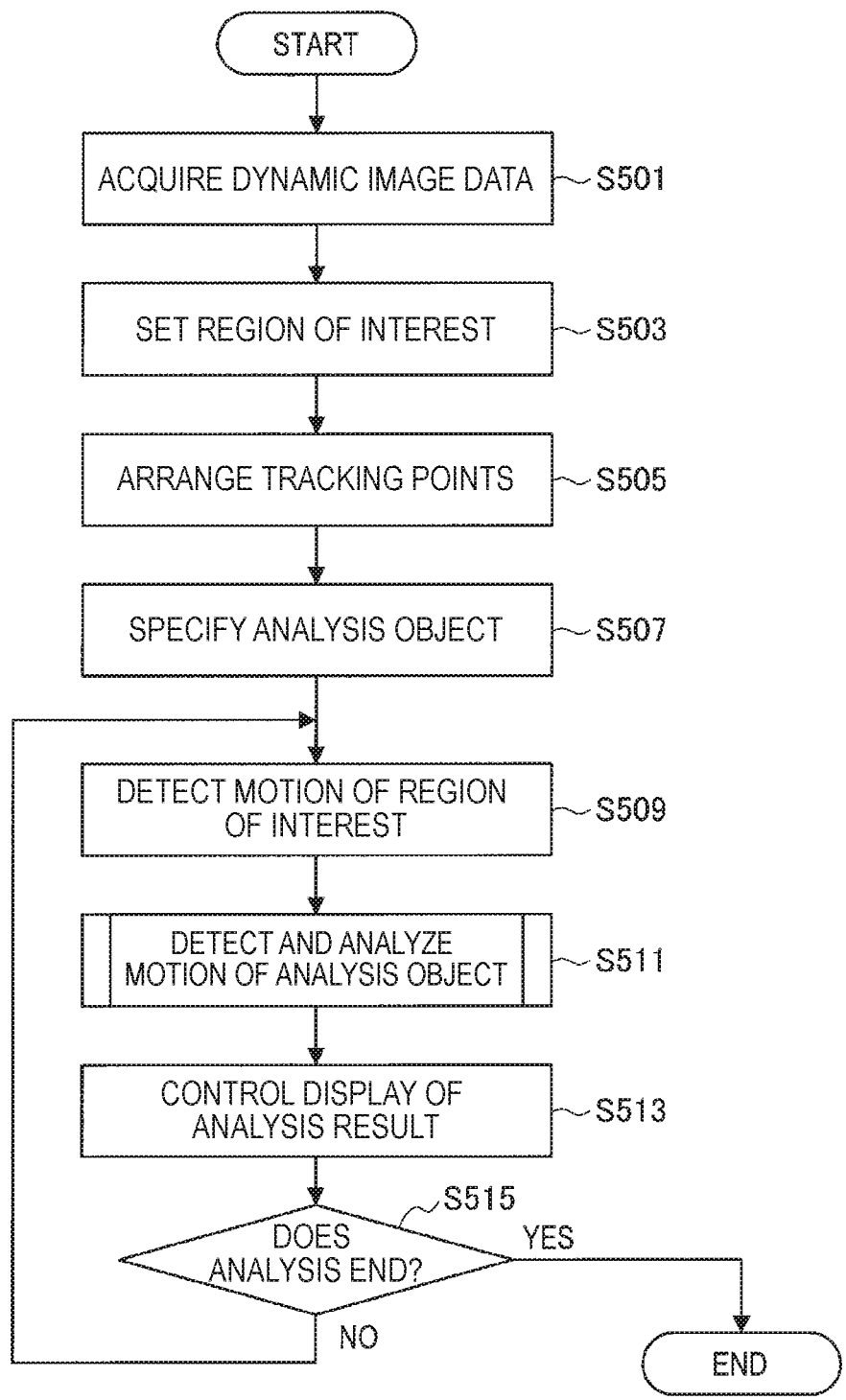
FIG. 22 is a flowchart illustrating an example of a process performed by an information processing device according to the embodiment.

FIG. 22 is a flowchart illustrating an example of a process by the information processing device 20 according to one embodiment of the present disclosure. First, the control unit 200 acquires dynamic image data from the imaging device 10 via the communication unit 210 (S501).

Then, the setting unit 201 extracts one captured image from the acquired dynamic image data and sets at least one region of interest from one captured image (S503). Then, the setting unit 201 arranges the tracking points on the contour line of the region of interest (S505).

Then, the analysis object specifying unit 202 specifies the analysis object for the region of interest (S507). The analysis object specified here is at least either of the two measurement points or the inside (mesh) of the region of interest. Further, in a case in which the analysis object specifying unit 202 specifies the two measurement points on the basis of the change in the shape of the region of interest, the analysis object is not specified at a time point of step S507. Instead, in step S603 to be described later, the two measurement points serving as the analysis objects are specified.

Then, the detection unit 203 (the region-of-interest motion detection unit 231) detects the motion of the region of interest in the dynamic image (S509). Then, the detection unit 203 (the analysis object motion detection unit 232) detects the motion of the analysis object in the dynamic image, and the analysis unit 204 analyzes the strain on the basis of the detected motion of the analysis object (S511). Here, content of the process in step S511 changes, depending on the analysis object specified in step S507.

Figure 23:
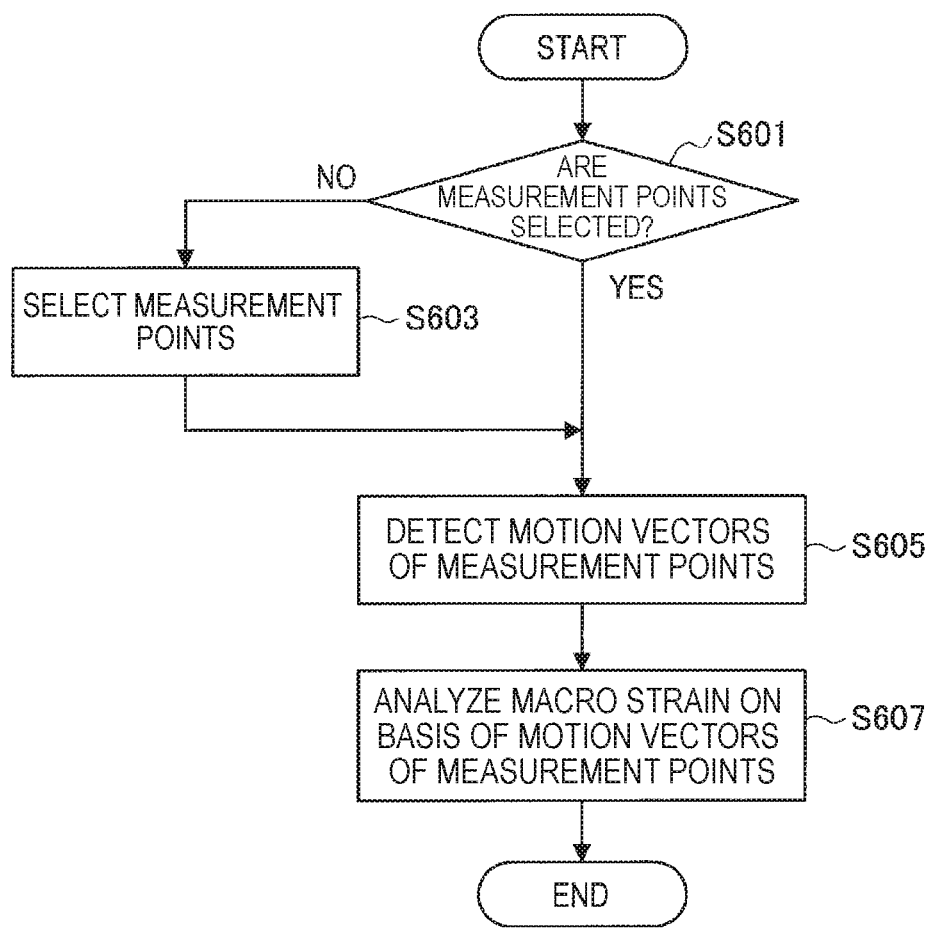
FIG. 23 is a flowchart illustrating an example of a process related to step S511 in a case in which two measurement points are specified as analysis objects.

First, an example in which the analysis object specifying unit 202 specifies the two measurement points as the analysis object will be described. FIG. 23 is a flowchart illustrating an example of a process related to step S511 in a case in which the two measurement points are specified as the analysis object. Referring to FIG. 23, first, in step S507, a process in a case in which the analysis object is not specified is performed (S601). More specifically, in a case in which the analysis object specifying unit 202 does not specify the two measurement points serving as the analysis object in step S507 (NO in S601), the analysis object specifying unit 202 specifies the two measurement points on the basis of the change in the shape of the region of interest (S603). Then, the analysis object motion detection unit 232 detects the motion vectors of the two measurement points (S605). Then, the analysis unit 204 analyzes the macro strain of the observation object on the basis of the detected motion vectors of the two measurement points (S607).

Figure 24:
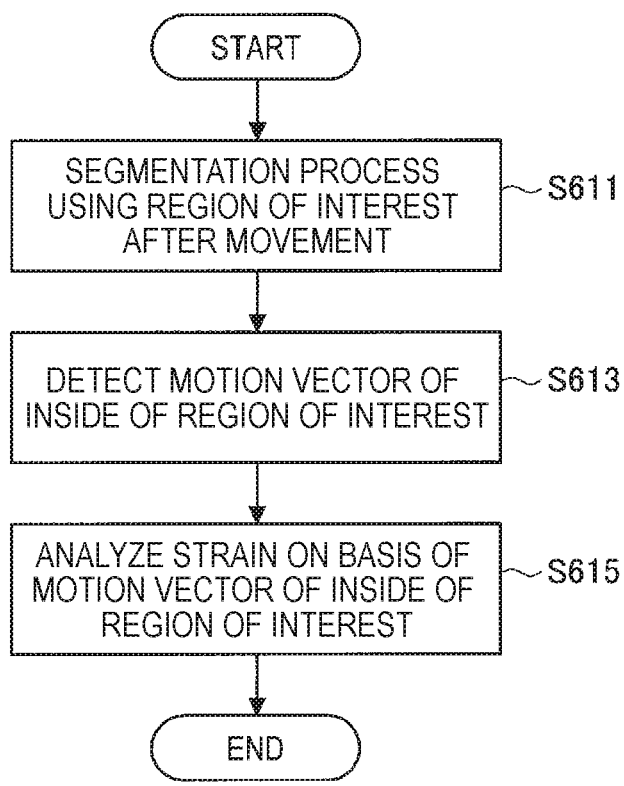
FIG. 24 is a flowchart illustrating an example of a process related to step S511 in a case in which the inside of a region of interest is specified as an analysis object.

Next, an example in which the analysis object specifying unit 202 specifies the inside (mesh) of the region of interest as the analysis object will be described. FIG. 24 is a flowchart illustrating an example of a process related to step S511 in a case in which the inside of region of interest is specified as the analysis object. Referring to FIG. 24, first, the analysis object specifying unit 202 performs the segmentation process (and the mesh process) using the region of interest in which the detection result by the detection unit 203 is reflected, and specifies the inside of the region of interest as the analysis object (S611). Then, the detection unit 203 detects the motion vector of the inside of the region of interest (S613). Then, the analysis unit 204 analyzes the macro strain or the micro strain of the observation object on the basis of the motion vector of the inside of the detected region of interest (S615).

The specific examples of the process related to step S511 have been described above. Referring again to FIG. 22, the display control unit 205 controls the display of the information related to the strain analyzed by the analysis unit 204 (S513). Thereafter, the control unit 200 determines whether or not the analysis processes ends (S515). In a case in which the analysis process continues (NO in S515), the process related to step S509 is performed again.

<2.3. Effect>

The configuration example and the process examples of the information processing device 20 according to one embodiment of the present disclosure have been described above. The information processing device 20 according to the present embodiment specifies the analysis object for the region of interest, detects the motion of the specified analysis object, and analyzes the strain of the observation object related to the region of interest on the basis of the detected motion of the analysis object. With this configuration, it is possible to analyze both the macro strain and the micro strain related to the contraction or relaxation of the observation object by detecting the motion of the analysis object specified for the observation object and tracking the motion. Accordingly, it is possible to obtain the strain related to the periodic change in the form of the observation object and the strain of the region contributing to the change in the form of the observation object. Therefore, it is possible to analyze the strain of observation object with a high degree of accuracy.

Further, the information processing device 20 according to the present embodiment can analyze the strain while tracking the change in the form of the observation object by detecting the tracking points and the motion of the analysis object. In other words, it is possible to analyze the strain without performing direct image recognition on the observation object for each captured image. Therefore, the computational cost can be suppressed.

Further, the information processing device 20 according to the present embodiment can control the display form of the information related to the analyzed strain on the basis of the motion of the analysis object or the motion of the region of interest. Accordingly, since the display form of the information related to the strain changes in accordance with the contraction or relaxation of the observation object, it is possible to easily detect a relation between the strain and the beat of the observation object.

«3. Hardware Configuration Example»

Figure 25:
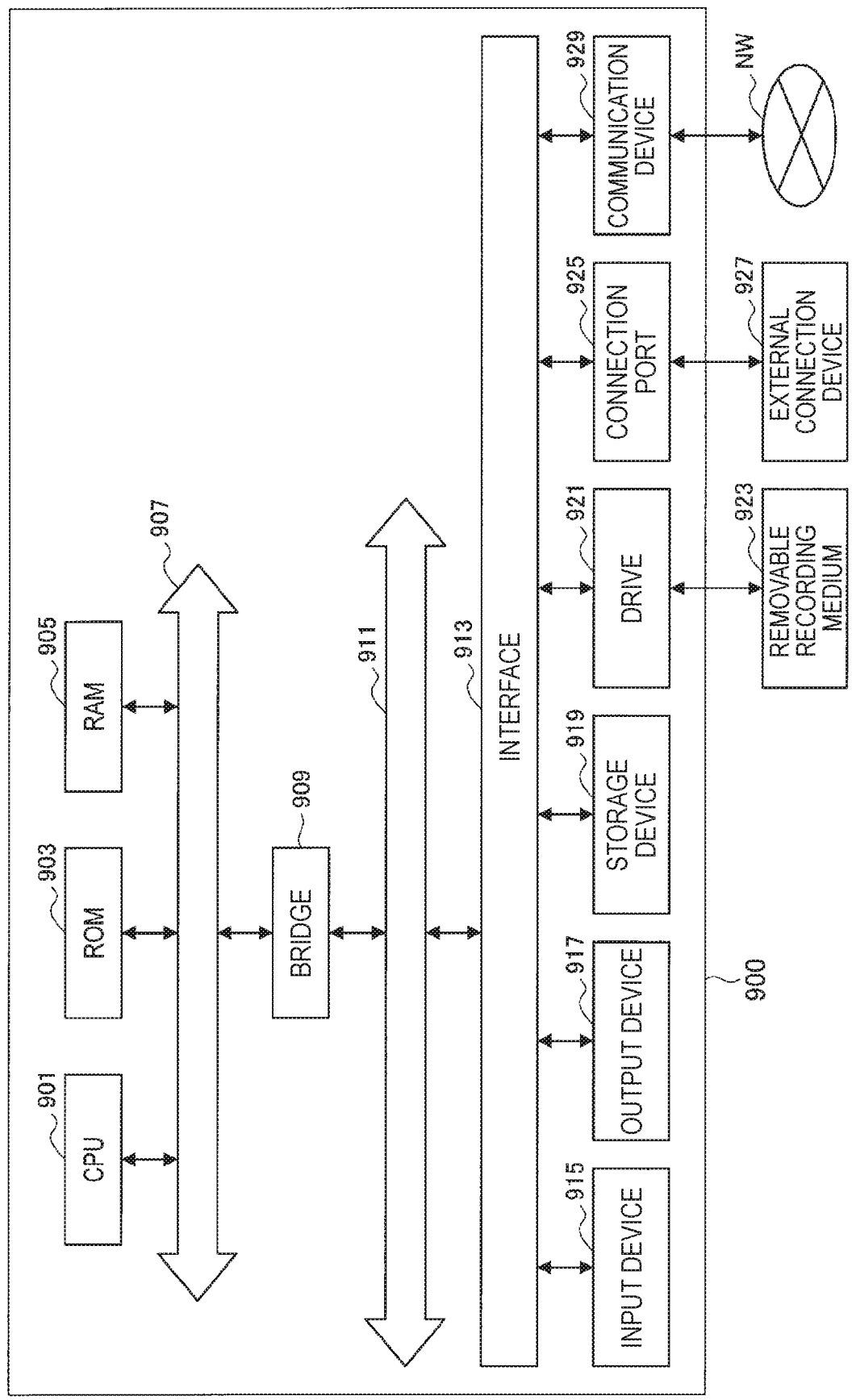
FIG. 25 is a block diagram showing a hardware configuration example of an information processing device according to an embodiment of the present disclosure.

Next, with reference to FIG. 25, a hardware configuration of an information processing device according to an embodiment of the present disclosure is described. FIG. 25 is a block diagram showing a hardware configuration example of the information processing device according to the embodiment of the present disclosure. An illustrated information processing device 900 can realize the information processing device 20 in the above described embodiment.

The information processing device 900 includes a CPU 901, read only memory (ROM) 903, and random access memory (RAM) 905. In addition, the information processing device 900 may include a host bus 907, a bridge 909, an external bus 911, an interface 913, an input device 915, an output device 917, a storage device 919, a drive 921, a connection port 925, and a communication device 929. The information processing device 900 may include a processing circuit such as a digital signal processor (DSP) or an application-specific integrated circuit (ASIC), instead of or in addition to the CPU 901.

The CPU 901 functions as an arithmetic processing device and a control device, and controls the overall operation or a part of the operation of the information processing device 900 according to various programs recorded in the ROM 903, the RAM 905, the storage device 919, or a removable recording medium 923. For example, the CPU 901 controls overall operations of respective function units included in the information processing device 20 of the above-described embodiment. The ROM 903 stores programs, operation parameters, and the like used by the CPU 901. The RAM 905 transiently stores programs used when the CPU 901 is executed, and parameters that change as appropriate when executing such programs. The CPU 901, the ROM 903, and the RAM 905 are connected with each other via the host bus 907 configured from an internal bus such as a CPU bus or the like. The host bus 907 is connected to the external bus 911 such as a Peripheral Component Interconnect/Interface (PCI) bus via the bridge 909.

The input device 915 is a device operated by a user such as a mouse, a keyboard, a touchscreen, a button, a switch, and a lever. The input device 915 may be a remote control device that uses, for example, infrared radiation and another type of radio waves. Alternatively, the input device 915 may be an external connection device 927 such as a mobile phone that corresponds to an operation of the information processing device 900. The input device 915 includes an input control circuit that generates input signals on the basis of information which is input by a user to output the generated input signals to the CPU 901. The user inputs various types of data and indicates a processing operation to the information processing device 900 by operating the input device 915.

The output device 917 includes a device that can visually or audibly report acquired information to a user. The output device 917 may be, for example, a display device such as an LCD, a PDP, and an OLED, an audio output device such as a speaker and a headphone, and a printer. The output device 917 outputs a result obtained through a process performed by the information processing device 900, in the form of text or video such as an image, or sounds such as audio sounds.

The storage device 919 is a device for data storage that is an example of a storage unit of the information processing device 900. The storage device 919 includes, for example, a magnetic storage device such as a hard disk drive (HDD), a semiconductor storage device, an optical storage device, or a magneto-optical storage device. The storage device 919 stores therein the programs and various data executed by the CPU 901, and various data acquired from an outside. Further, the storage device 919 can realize the function of the storage unit 220 according to the above embodiments.

The drive 921 is a reader/writer for the removable recording medium 923 such as a magnetic disk, an optical disc, a magneto-optical disk, and a semiconductor memory, and built in or externally attached to the information processing device 900. The drive 921 reads out information recorded on the mounted removable recording medium 923, and outputs the information to the RAM 905. The drive 921 writes the record into the mounted removable recording medium 923.

The connection port 925 is a port used to directly connect devices to the information processing device 900. The connection port 925 may be a Universal Serial Bus (USB) port, an IEEE1394 port, or a Small Computer System Interface (SCSI) port, for example. The connection port 925 may also be an RS-232C port, an optical audio terminal, a High-Definition Multimedia Interface (HDMI (registered trademark)) port, and so on. The connection of the external connection device 927 to the connection port 925 makes it possible to exchange various kinds of data between the information processing device 900 and the external connection device 927.

The communication device 929 is a communication interface including, for example, a communication device for connection to a communication network NW. The communication device 929 may be, for example, a wired or wireless local area network (LAN), Bluetooth (registered trademark), or a communication card for a wireless USB (WUSB). The communication device 929 may also be, for example, a router for optical communication, a router for asymmetric digital subscriber line (ADSL), or a modem for various types of communication. For example, the communication device 929 transmits and receives signals in the Internet or transits signals to and receives signals from another communication device by using a predetermined protocol such as TCP/IP. The communication network NW to which the communication device 929 connects is a network established through wired or wireless connection. The communication network NW is, for example, the Internet, a home LAN, infrared communication, radio wave communication, or satellite communication. Further, at least one of the connection port 925 and the communication device 929 can realize the function of the communication unit 210 according to the above embodiments.

The example of the hardware configuration of the information processing device 900 has been introduced.

«4. Conclusion»

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, although the information processing system 1 is configured to be provided with the imaging device 10 and information processing device 20 in the above-described embodiment, the present technology is not limited thereto. For example, the imaging device 10 may have the function of the information processing device 20 (a setting function, an analysis object specifying function, a detection function, and an analysis function). In this case, the information processing system 1 is realized by the imaging device 10. In addition, the information processing device 20 may have the function of the imaging device 10 (imaging function). In this case, the information processing system 1 is realized by the information processing device 20. Further, the imaging device 10 may have a part of the function of the information processing device 20, and the information processing device 20 may have a part of the function of the imaging device 10.

The steps in the processes performed by the information processing device in the present specification may not necessarily be processed chronologically in the orders described in the flowcharts. For example, the steps in the processes performed by the information processing device may be processed in different orders from the orders described in the flowcharts or may be processed in parallel.

Also, a computer program causing hardware such as the CPU, the ROM, and the RAM included in the information processing device to carry out the equivalent functions as the above-described configuration of the information processing device can be generated. Also, a storage medium having the computer program stored therein can be provided.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing device, including:

a setting unit configured to set at least one region of interest from one captured image constituting a dynamic image for a biological sample;

an analysis object specifying unit configured to specify an analysis object for the at least one region of interest;

a detection unit configured to detect a motion of the analysis object in the dynamic image; and an analysis unit configured to analyze a strain of the biological sample related to the at least one region of interest on a basis of the detected motion of the analysis object.

(2)

The information processing device according to (1), in which the analysis object specifying unit specifies two measurement points on a contour line of the at least one region of interest, as the analysis object, the detection unit detects motions of the two measurement points in the dynamic image, and the analysis unit analyzes the strain on a basis of the motions of the two measurement points.

(3)

The information processing device according to (2), in which the analysis object specifying unit specifies arrangement positions of the two measurement points on a basis of a shape of the contour line.

(4)

The information processing device according to (2) or (3), in which the analysis object specifying unit specifies arrangement positions of the two measurement points on a basis of a change in a shape of the contour line in the dynamic image.

(5)

The information processing device according to any one of (1) to (4), in which the analysis object specifying unit specifies an inside of the at least one region of interest as the analysis object, the detection unit detects a motion of the inside of the at least one region of interest in the dynamic image, and the analysis unit analyzes the strain on a basis of the motion of the inside of the at least one region of interest.

(6)

The information processing device according to (5), in which the analysis unit calculates an affine parameter of the motion of the inside of the at least one region of interest detected by the detection unit and analyzes the strain on a basis of the affine parameter.

(7)

The information processing device according to any one of (1) to (6), in which the detection unit is able to further detect a motion of the at least one region of interest, and in the detection unit, a motion detector used for detecting the motion of the analysis object is different from a motion detector used for detecting the motion of the at least one region of interest.

(8)

The information processing device according to any one of (1) to (7), in which the analysis unit analyzes the strain on a basis of a temporal change in the motion of the analysis object.

(9)

The information processing device according to any one of (1) to (8), further including a display control unit configured to control display of information related to the strain analyzed by the analysis unit.

(10)

The information processing device according to (9), in which the display control unit controls a display form of the information related to the strain in accordance with the motion of the analysis object.

(11)

The information processing device according to (10), in which the display control unit controls the display form of information related to the strain by using a beat center estimated for the at least one region of interest.

(12)

The information processing device according to any one of (9) to (11), in which the display control unit controls the display form of the information related to the strain in accordance with a change in a shape of the contour line of the at least one region of interest in the dynamic image.

(13)

The information processing device according to any one of (9) to (12), in which the display control unit controls the display form of the information related to the strain on a basis of a magnitude of the motion of the analysis object.

(14)

The information processing device according to any one of (1) to (13), in which the strain includes a strain indicating a dynamic characteristic related to contraction or relaxation of the entire biological sample.

(15)

The information processing device according to any one of (1) to (14), in which the strain includes a strain indicating a local dynamic characteristic inside the biological sample.

(16)

The information processing device according to any one of (1) to (15), in which the setting unit sets a region corresponding to the biological sample included in the one captured image as the at least one region of interest.

(17)

The information processing device according to any one of (1) to (16), in which the biological sample is a biological sample that performs periodic movement.

(18)

An information processing method, including:

setting, by a processor, at least one region of interest from one captured image constituting a dynamic image for a biological sample;

specifying, by the processor, an analysis object for the at least one region of interest;

detecting, by the processor, a motion of the analysis object in the dynamic image; and analyzing, by the processor, a strain of the biological sample related to the at least one region of interest on a basis of the detected motion of the analysis object.

(19)

A program causing a computer to function as:

a setting unit configured to set at least one region of interest from one captured image constituting a dynamic image for a biological sample;

an analysis object specifying unit configured to specify an analysis object for the at least one region of interest;

a detection unit configured to detect a motion of the analysis object in the dynamic image; and an analysis unit configured to analyze a strain of the biological sample related to the at least one region of interest on a basis of the detected motion of the analysis object.

(20)

An information processing system, including:

an imaging device including an imaging unit configured to generate a dynamic image of a biological sample; and an information processing device including a setting unit configured to set at least one region of interest from one captured image constituting the dynamic image, an analysis object specifying unit configured to specify an analysis object for the at least one region of interest, a detection unit configured to detect a motion of the analysis object in the dynamic image, and an analysis unit configured to analyze a strain of the biological sample related to the at least one region of interest on a basis of the detected motion of the analysis object.

REFERENCE SIGNS LIST 1 information processing system
10 imaging device
20 information processing device
200 control unit
201 setting unit
202 analysis object specifying unit
203 detection unit
204 analysis unit
205 display control unit
210 communication unit
220 storage unit
231 region-of-interest motion detection unit
232 analysis object motion detection unit

The invention claimed is:

1. An information processing device, comprising:
a processor configured to:
set at least one region of interest from a first captured image of a dynamic image of a biological sample;
specify an analysis object for the at least one region of interest;
detect a motion of the analysis object in the dynamic image based on the at least one region of interest from the first captured image as a reference for a second captured image of the dynamic image;
analyze a strain of the biological sample related to the at least one region of interest based on the detected motion of the analysis object; and
control display of information related to the strain across a plurality of regions of the biological sample, such that a strength of the strain in a first region of the plurality of regions is visually distinguishable from the strength of the strain in a second region of the plurality of regions.

2. The information processing device according to claim 1, wherein the processor is further configured to:
specify two measurement points on a contour line of the at least one region of interest, as the analysis object;
detect motions of the two measurement points in the dynamic image; and
analyze the strain based on the motions of the two measurement points.

3. The information processing device according to claim 2, wherein the processor is further configured to specify arrangement positions of the two measurement points based on a shape of the contour line.

4. The information processing device according to claim 2, wherein the processor is further configured to specify arrangement positions of the two measurement points based on a change in a shape of the contour line in the dynamic image.

5. The information processing device according to claim 1, wherein the processor is further configured to:
specify an inside of the at least one region of interest as the analysis object;
detect a motion of the inside of the at least one region of interest in the dynamic image; and
analyze the strain based on the motion of the inside of the at least one region of interest.

6. The information processing device according to claim 5, wherein the processor is further configured to:
calculate an affine parameter of the motion of the inside of the at least one region of interest; and
analyze the strain based on the affine parameter.

7. The information processing device according to claim 1, wherein
the processor is further configured to detect a motion of the at least one region of interest, and a motion detector used for the detection of the motion of the analysis object is different from a motion detector used for detection of the motion of the at least one region of interest.

8. The information processing device according to claim 1, wherein the processor is configured to analyze the strain based on a temporal change in the motion of the analysis object.

9. The information processing device according to claim 1, further comprising a display device configured to display the information related to the strain.

10. The information processing device according to claim 9, wherein the processor is further configured to control a display form of the information related to the strain in accordance with the motion of the analysis object.

11. The information processing device according to claim 10, wherein the processor is further configured to control the display form of the information related to the strain based on a beat center estimated for the at least one region of interest.

12. The information processing device according to claim 10, wherein the processor is further configured to control the display form of the information related to the strain in accordance with a change in a shape of a contour line of the at least one region of interest in the dynamic image.

13. The information processing device according to claim 10, wherein the processor is further configured to control the display form of the information related to the strain based on a magnitude of the motion of the analysis object.

14. The information processing device according to claim 1, wherein the strain indicates a dynamic characteristic related to contraction or relaxation of the biological sample.

15. The information processing device according to claim 1, wherein the strain indicates a local dynamic characteristic inside the biological sample.

16. The information processing device according to claim 1, wherein the processor is further configured to set a region corresponding to the biological sample included in the first captured image as the at least one region of interest.

17. The information processing device according to claim 1, wherein the biological sample is a biological sample that performs periodic movement.

18. An information processing method, comprising:
setting, by a processor, at least one region of interest from a first captured image of a dynamic image of a biological sample;
specifying, by the processor, an analysis object for the at least one region of interest;
detecting, by the processor, a motion of the analysis object in the dynamic image based on the at least one region of interest from the first captured image as a reference for a second captured image of the dynamic image;
analyzing, by the processor, a strain of the biological sample related to the at least one region of interest based on the detected motion of the analysis object; and
controlling, by the processor, display of information related to the strain across a plurality of regions of the biological sample, such that a strength of the strain in a first region of the plurality of regions is visually distinguishable from the strength of the strain in a second region of the plurality of regions.

19. A non-transitory computer-readable medium having stored thereon, computer-executable instructions which, when executed by a computer, cause the computer to execute operations, the operations comprising:
setting at least one region of interest from a first captured image of a dynamic image of a biological sample;
specifying an analysis object for the at least one region of interest;
detecting a motion of the analysis object in the dynamic image based on the at least one region of interest from the first captured image as a reference for a second captured image of the dynamic image;
analyzing a strain of the biological sample related to the at least one region of interest based on the detected motion of the analysis object; and
controlling display of information related to the strain across a plurality of regions of the biological sample, such that a strength of the strain in a first region of the plurality of regions is visually distinguishable from the strength of the strain in a second region of the plurality of regions.

20. An information processing system, comprising:
an imaging device configured to generate a dynamic image of a biological sample; and
an information processing device configured to:
set at least one region of interest from a first captured image of the dynamic image;
specify an analysis object for the at least one region of interests;
detect a motion of the analysis object in the dynamic image based on the at least one region of interest from the first captured image as a reference for a second captured image of the dynamic image; and
analyze a strain of the biological sample related to the at least one region of interest based on the detected motion of the analysis object; and
control display of information related to the strain across a plurality of regions of the biological sample, such that a strength of the strain in a first region of the plurality of regions is visually distinguishable from the strength of the strain in a second region of the plurality of regions.

* * * * *